US007332615B2

(12) United States Patent
Huang et al.

(10) Patent No.: US 7,332,615 B2
(45) Date of Patent: Feb. 19, 2008

(54) HYDROPHILIC ANALOGS OF 4,8-DIHYDROBENZODITHIOPHENE-4,8-DIONES AS ANTICANCER AGENTS

(75) Inventors: Pi-Tsan Huang, Hsinchu (TW); Yen-Fang Wen, Hsinchu (TW); Wuu-Chian Shin, Hsinchu (TW); Mei-Hwai Chen, Hsinchu (TW); Sheng-Chu Kuo, Taichung (TW); Kuo-Hsiung Lee, Chapel Hill, NC (US)

(73) Assignees: Industrial Technology Research Institute, Hsinchu (TW); Yung Shin Pharm. Ind. Co., Ltd., Taichung (TW)

( * ) Notice: Subject to any disclaimer, the term of this patent is extended or adjusted under 35 U.S.C. 154(b) by 15 days.

(21) Appl. No.: 11/236,730

(22) Filed: Sep. 28, 2005

(65) Prior Publication Data

US 2006/0069041 A1 Mar. 30, 2006

Related U.S. Application Data

(60) Provisional application No. 60/613,225, filed on Sep. 28, 2004.

(51) Int. Cl.
*A61K 31/38* (2006.01)
*C07D 333/74* (2006.01)

(52) U.S. Cl. ........................... 549/43; 549/44; 549/45; 549/48; 514/443

(58) Field of Classification Search .................. 549/43, 549/44, 45, 48; 514/443
See application file for complete search history.

(56) References Cited

U.S. PATENT DOCUMENTS

| | | | |
|---|---|---|---|
| 5,919,816 A * | 7/1999 | Hausheer et al. | 514/449 |
| 6,174,913 B1 * | 1/2001 | Lee et al. | 514/443 |
| 6,696,416 B1 * | 2/2004 | Mazar et al. | 514/16 |

* cited by examiner

*Primary Examiner*—Shaojia Anna Jiang
*Assistant Examiner*—Traviss McIntosh
(74) *Attorney, Agent, or Firm*—Bacon & Thomas PLLC

(57) ABSTRACT

The present invention discloses hydrophilic derivatives of 4,8-dihydrobenzodithiophene-4,8-diones, which are active as anticancer agents, along with pharmaceutical formulations containing the same.

19 Claims, No Drawings

HYDROPHILIC ANALOGS OF 4,8-DIHYDROBENZODITHIOPHENE-4,8-DIONES AS ANTICANCER AGENTS

CROSS-REFERENCE TO RELATED APPLICATION

This application claims the benefit of U.S. Provisional Application No. 60/613,225, filed 28 Sep. 2004.

FIELD OF THE INVENTION

The present invention concerns hydrophilic analogs of 4,8-dihydrobenzodithiophene-4,8-diones, which are active as anticancer agents, along with pharmaceutical formulations containing the same.

BACKGROUND OF THE INVENTION

In our prior studies, naphtho[2,3-b]thiophene4,9-diones (A), 4,8-dihydrobenzo[1,2-b: 5,4-b']dithiophene-4,8-diones (B) and, 4,8-dihydrobenzo[1,2-b: 4,5-b']dithiophene-4,8-diones(C) were identified as potential anticancer agents [U.S. Pat. Nos. 6,174,913 B1; 6,337,346B1, details of which are incorporated herein by reference]. Among these benzothiophene analogs, many compounds possessed very potent cytotoxic activity against human tumor cell lines. However, most of these compounds were quite lipophilic, and therefore, not optimal for in vivo and clinical studies.

(A)

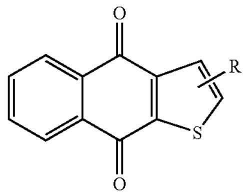

(B)

(C)

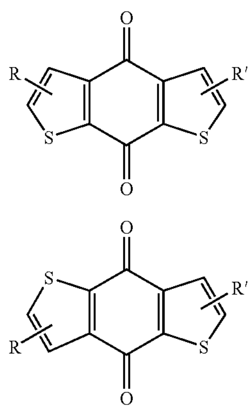

SUMMARY OF THE INVENTION

The present invention was undertaken to synthesize novel hydrophilic analogs of dihydrobenzodithiophenediones and to evaluate their anticancer activity.

A first aspect of the present invention is a compound selected from the group consisting of compounds of formula (D) and compounds of formula (E):

(D)

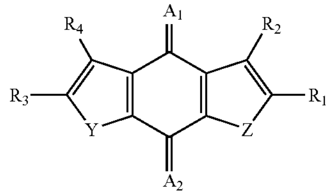

(E)

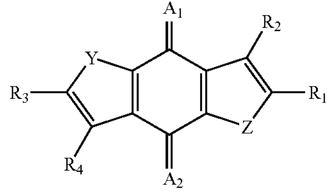

wherein Y and Z independently are O, S, —NH—, or Se, and preferably Y and Z are S;

$A_1$ and $A_2$ independently are O, S, or $NR_5$, wherein $R_5$ is H or alkyl;

$R_1$, $R_2$, $R_3$ and $R_4$ independently are H, alkyl, $—CR_5R_6—X—C(O)—(CH_2)_nCOOH$, $—CR_5R_6—X—(CH_2)_nCOOH$, $—CR_5R_6—X—(CH_2)_nNR_5R_6$, $—C(O)—NR_6—(CR_5R_6)_nCOOH$, $—C(O)—NR_6—(CR_5R_6)_nNR_5R_6$, $—CR_5R_6—C(O)—(CH_2)_nCOOH$, $—CR_5R_6—X—C(O)—(CH_2)_nNR_5R_6$, $—C(O)—(CR_5R_6)_nCOOH$, $—C(O)—(CR_5R_6)_nNR_5R_6$, $—CR_5{=}N—(CH_2)_nCOOH$, $—CR_5{=}N—(CH_2)_nNR_5R_6$, $—CR_5{=}NOH$, or

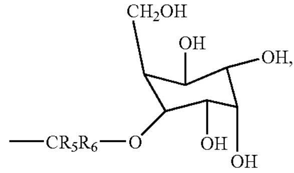

wherein X is O, S, or NH; $R_5$ is defined as above; $R_5$ is H or alkyl; and n is 1-5; subject to the proviso that at least one of $R_1$, $R_2$, $R_3$ and $R_4$ is a radical other than hydrogen and alkyl; or a pharmaceutically acceptable salt thereof.

Preferably, $R_2$, $R_3$ and $R_4$ are H, and $R_1$ is $—CR_5R_6—X—C(O)—(CH_2)_nCOOH$, $—CR_5R_6—X—(CH_2)_nCOOH$, $—CR_5R_6—X—(CH_2)_nNR_5R_6$, $—C(O)—NR_6—(CR_5R_6)_nCOOH$, or $—C(O)—NR_6—(CR_5R_6)_nNR_5R_6$, wherein X, $R_5$, $R_6$ and n are defined as above.

Preferably, $A_1$ and $A_2$ are O.

Preferably, X is O.

Preferably, $R_5$ and $R_6$ independently are H or methyl.

Preferably, $R_2$, $R_3$ and $R_4$ are H, and $R_1$ is $—CR_5R_6—X—C(O)—(CH_2)_nCOOH$, wherein X, $R_5$, $R_6$ and n are defined as above.

Preferably, $R_2$, $R_3$ and $R_4$ are H, and $R_1$ is $—CR_5R_6—X—(CH_2)_nCOOH$, wherein X, $R_5$, $R_6$ and n are defined as above.

Preferably, $R_2$, $R_3$ and $R_4$ are H, and $R_1$ is $—CR_5R_6—X—(CH_2)_nNR_5R_6$, wherein X, $R_5$, $R_6$ and n are defined as above.

Preferably, $R_2$, $R_3$ and $R_4$ are H, and $R_1$ is $—C(O)—NR_6—(CR_5R_6)_nCOOH$, wherein X, $R_5$, $R_6$ and n are defined as above.

Preferably, $R_2$, $R_3$ and $R_4$ are H, and $R_1$ is —C(O)—$NR_6$—$(CR_5R_6)_n NR_5R_6$, wherein X, $R_5$, $R_6$ and n are defined as above.

Preferably, the compound of the present invention has the formula (D).

Preferably, the compound of the present invention has the formula (E).

Preferably, the compound of the present invention has the formula (D) is mono-[1-(4,8-dioxo-4,8-dihydrobenzo[1,2-b:5,4-b']dithiophen-2-yl)-methyl]succinate (IIa-1), mono-[1-(4,8-dioxo-4,8-dihydrobenzo[1,2-b:5,4-b']dithiophen-2-yl) ethyl]succinate (IIb-1), or mono-[1-(4,8-dioxo-4,8-dihydrobenzo[1,2-b:5,4-b']dithiophen-2-yl)-ethyl] pentanedioate (IIb-2); and the compound of the present invention has the formula (E) is mono-[1-(4,8-dioxo-4,8-dihydroxybenzo[1,2-b;4,5-b']dithiophen-2-yl)-ethyl]succinate (VII-1), mono-[1-(4,8-dioxo-4,8-dihydroxybenzo[1,2-b;4,5-b']dithiophen-2-yl)-ethyl]pentanedioate (VII-2), or 4,8-dioxo-4,8-dihydrobenzo[1,2-b;4,5-b']dithiophene-2-carboxylate-(2-dimethylamino-ethyl)-amide (XV-2).

A second aspect of the present invention is a composition comprising an effective anticancer amount of a compound of the formula (D) or (E) above, or a pharmaceutically acceptable salt thereof, in a pharmaceutically acceptable carrier.

A further aspect of the present invention is a method for treating a tumor, the method comprising administering to a subject in need of treatment a compound of the formula (D) or (E) above, or a pharmaceutically acceptable salt thereof, in an amount effective to treat said tumor.

A still further aspect of the present invention is the use of a compound of the formula (D) or (E) above, or a pharmaceutically acceptable salt thereof, for the preparation of a medicament for carrying out the method described above.

Preferably, said tumor is selected from the group consisting of non-small cell lung cancer, breast cancer, nasopharynx carcinoma, prostate cancer, colon cancer, hepatoma, ileocecal carcinoma, leukemia and central nervous system cancers, and more preferably said tumor is non-small cell lung cancer, breast cancer, nasopharynx carcinoma and prostate cancer.

DETAILED DESCRIPTION OF THE INVENTION

As part of a continuing search for potential anticancer drug candidates in the benzodithiophenedione series, novel hydrophilic analogs were synthesized and evaluated. A series of succinates (D, E) and amides (XV) derived from hydroxyalkyl-4,8-dihydrobenzo[1,2-b:5,4-b']dithiophene-4,8-dione (I) and hydroxyalkyl-4,8-dihydrobenzo[1,2-b:4,5-b']dithiophene-4,8-dione (VI) are worthy of further exploration for their anticancer activities.

The term "alkyl" as used herein, inidividually or as a portion of another substituent term such as "alkoxy", refers to C1 to C4 alkyl, which may be linear or branched, and saturated or unsaturated. Preferably, the alkyl is saturated, and preferably the alkyl is linear.

The term "halogen" or "halo" as used herein refers to fluorine, chlorine, bromine, iodine, etc., or fluoro, chloro, bromo, iodo, etc., respectively.

Suitable methods for synthesizing the compounds of the present invention will be described in the following, and variations thereof will be apparent to those skilled in the art in given the Examples set forth below.

The key intermediates (I,VI) needed for the synthesis of target compounds were prepared according to our previously reported procedures [L. J. Huang, S. C. Kuo, C. Y. Perng, Y. H. Chao, T. S. Wu, A. T. Mcphail, A. Manger, H. Y. Cheng and K. H. Lee. Bioorg. Med. Chem. Lett 8, 2763-2768 (1998); Y. H. Chao, S. C. Kuo, C. H. Wu, C. Y. Lee, A. Manger, I. C. Sun, S. L. Morris-Natschke and K. H. Lee. J. Med. Chem. 41, 4658-4661 (1998); Y. H. Chao, S. C. Kuo, K. Ku, I. P. Chiu, C. H. Wu, A. Manger, H. K. Wang, and K. H. Lee. Bioorg. Med. Chem. 7, 1025-1031 (1999)].

As shown in Scheme 1. the mono-(4,8-dioxo-4,8-dihydrobenzo[1,2-b:5,4-b']dithiophenyl-alkyl)alkanedioates (II) were obtained by treating the key intermediate I, hydroxyalkyl-4,8-dihydrobenzo[1,2-b:5,4-b']dithiophene-4,8-diones, with anhydride in the presence of organic or inorganic base.

Scheme 1

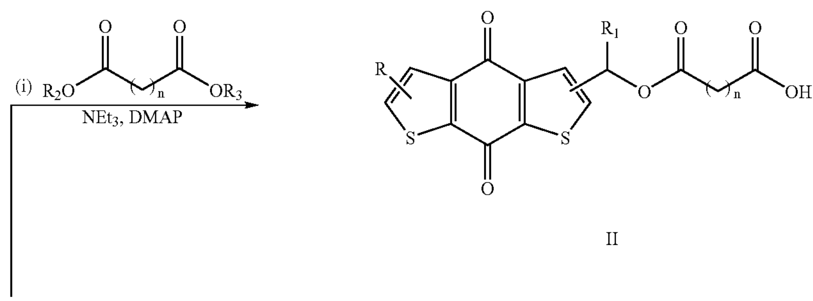

-continued

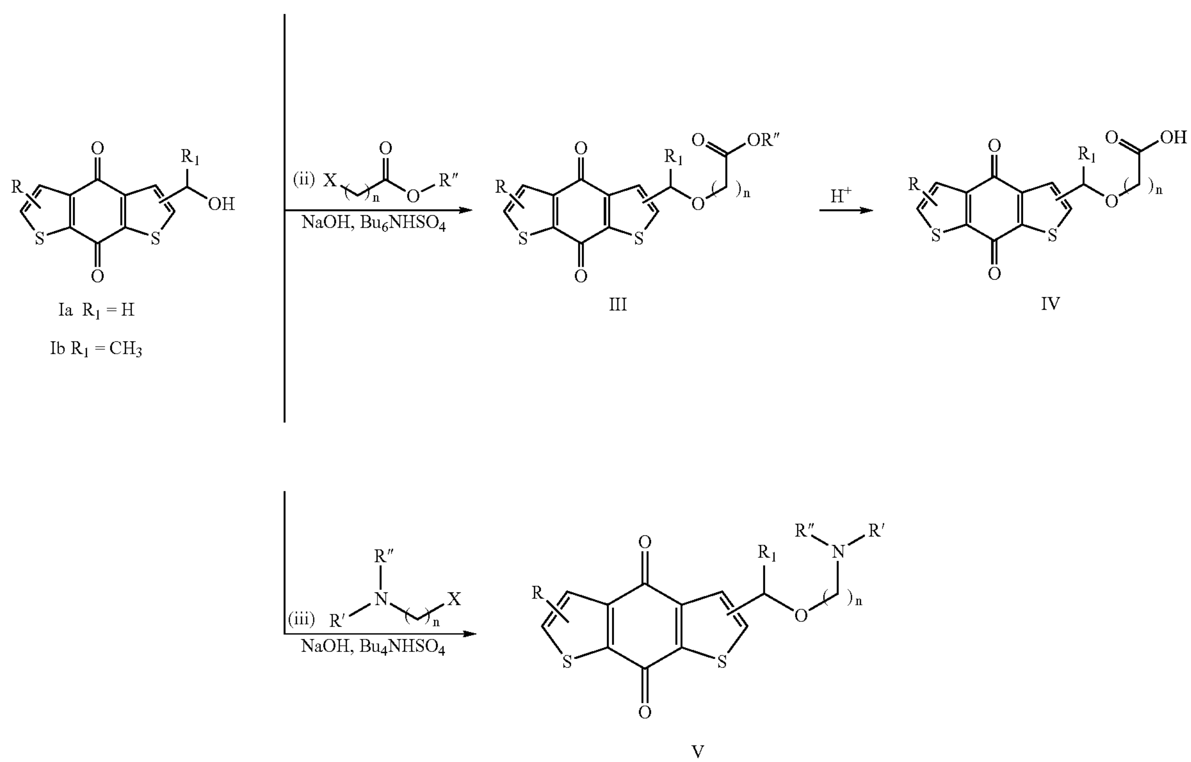

When the key intermediate I was reacted with a variety of haloalkanoates [$X(CH_2)nCOOEt$] in the presence of alkali, the corresponding alkoxyalkanoates (III) were obtained. Hydrolysis of compounding III with TFA or NaOH affords the corresponding acids (IV), which could be led to water soluble salts. Reaction of key intermediates I with a variety of haloalkylamines gave the corresponding alkoxyalkylamines (V), which could be treated with HCl, respectively, to afford their water soluble salts.

On the other hand, using the key intermediates VI, hydroxyalkyl-4,8-dihydrobenzo[1,2-b:4,5-b']dithiophene-4,8-diones, as starting materials, following the similar procedures (Scheme 2) described above for the preparation of compounds II, IV, V, we successfully converted the key intermediates VI into hydrophilic target compounds VII, IX, X.

Scheme 2

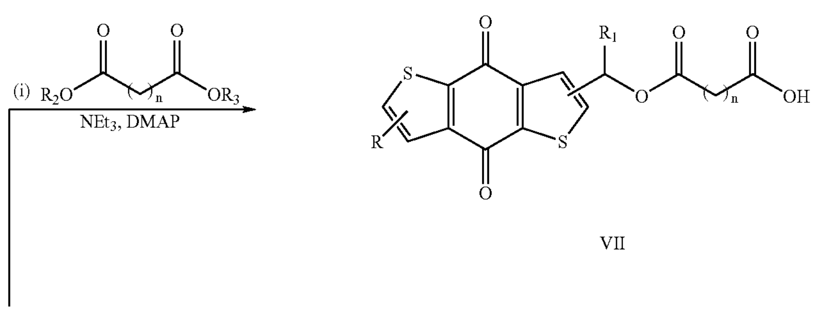

-continued

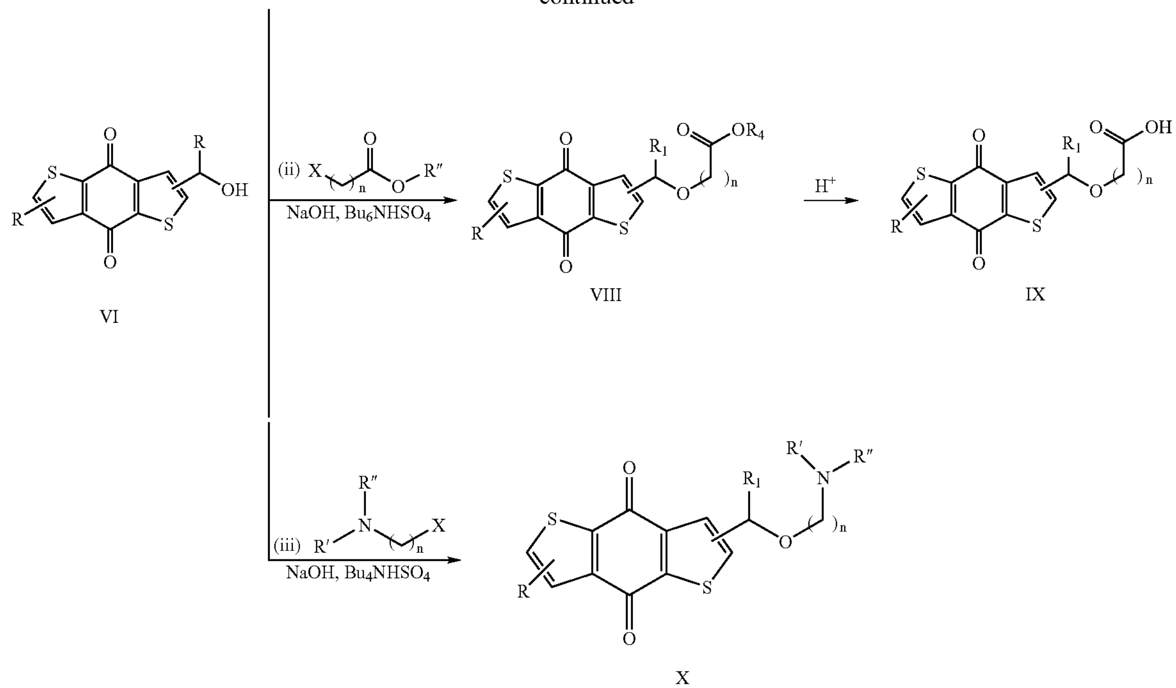

As shown in Scheme 3, the 4,8-dihydrobenzo[1,2-b:5,4-b']dithio-phene-4,8-dione-2-carboxylic acid XI was treated with amino acids in the presence of coupling agent to form the amides XII, which were then converted to the corresponding acids XIII. When XI was treated with $NH_3$, the corresponding ammonium salts (XI-$NH_4$) was obtained. On the other hand, compounds XI was allowed to react with $SOCl_2$ to afford the corresponding acid chloride, which was treated with a variety of aminoalkylamines to give corresponding amides (XVII) which could be treated with $H_3PO_4$ respectively to afford their water soluble salts (XVII-$H_3PO_4$).

Scheme 3

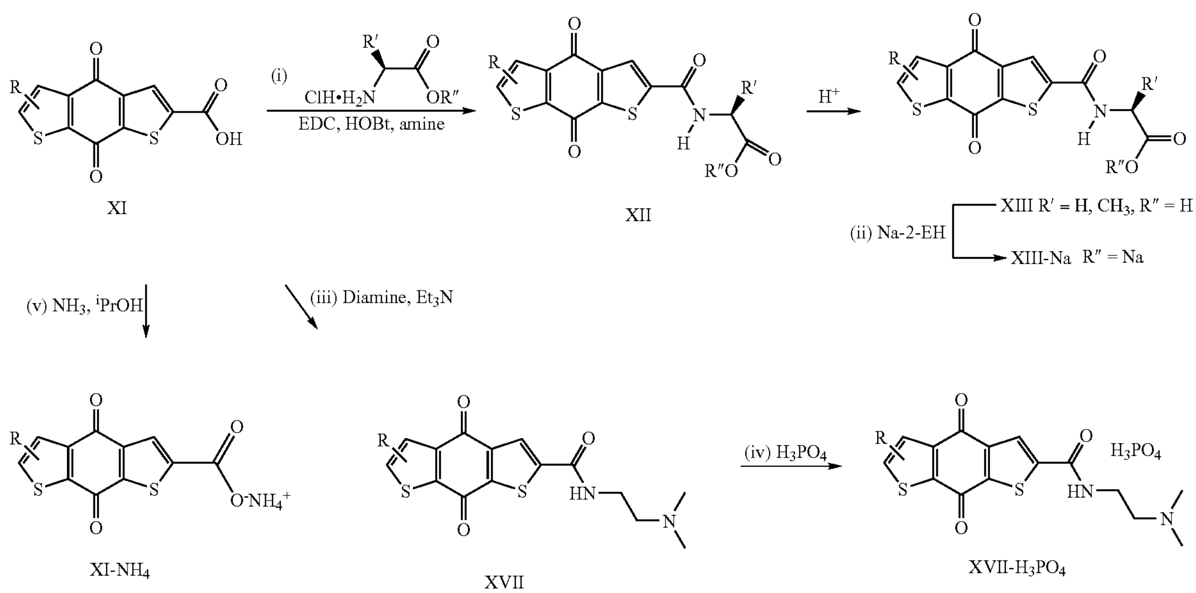

When the 4,8-dihydrobenzo[1,2-b:4,5-b']dithiophene-4.8-dione-2-carboxylic acids (XIV) were used as starting material following the similar procedures (Scheme 4) described above for the preparation of compounds XIII-Na, $XI\text{-}NH_4$ and $XVII\text{-}H_3PO_4$, we successfully converted the starting material XIV into target compounds XVI-Na and $XIV\text{-}NH_4$ and $XVII\text{-}H_3PO_4$.

Scheme 4

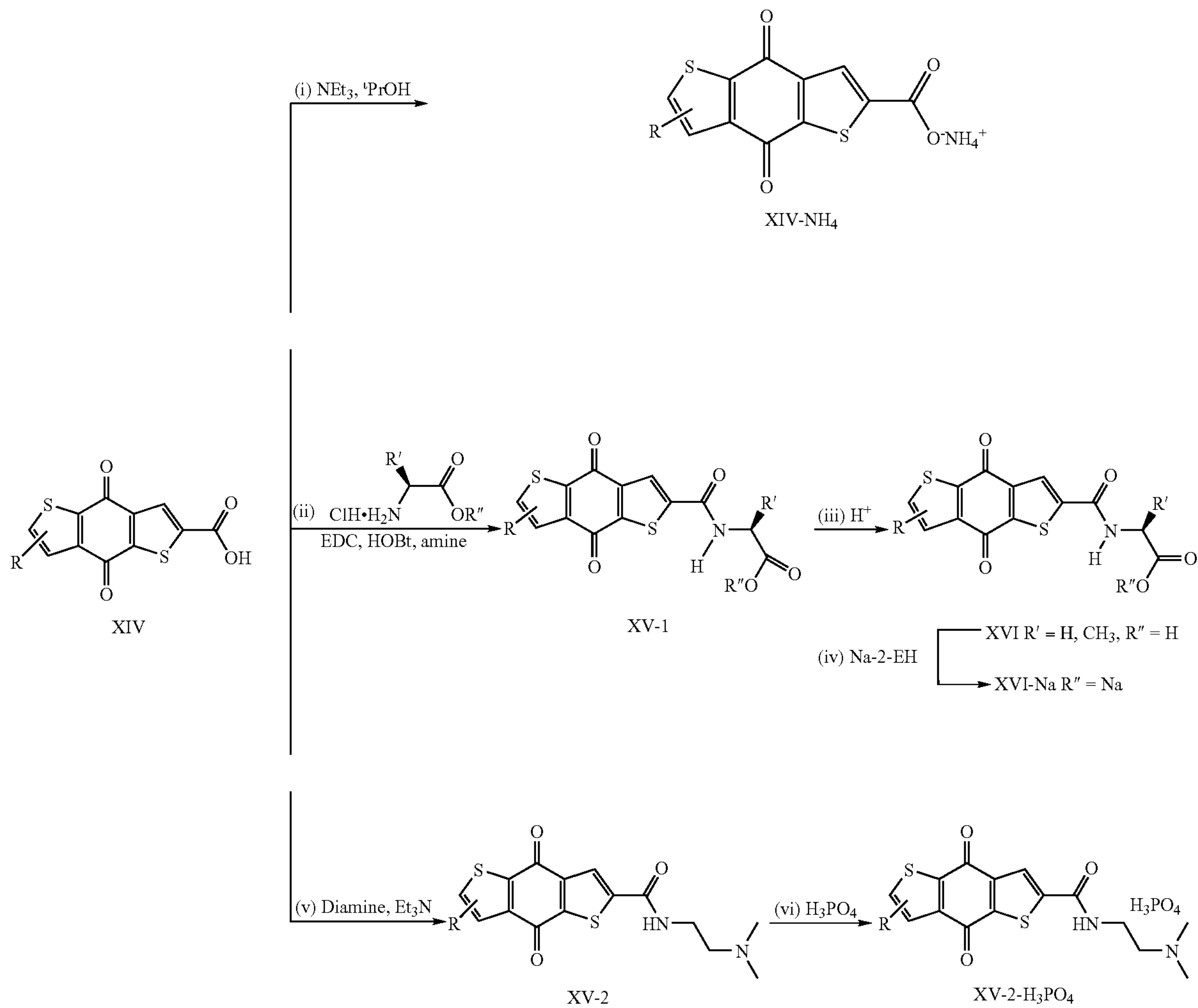

The following Examples are provided to further illustrate the present invention, and should not be construed as limiting thereof. All melting points were determined on a Büchi MP-540 apparatus and are uncorrected. NMR spectra were obtained on a Varian Unity Inova-500 spectrometer in DMSO-d6, $CD_3OD$ or $CDCl_3$. The chemical shift values are expressed in δ values (parts per million). The following abbreviations are used: s=singlet, d=doublet, t=triplet, q=quartet, m=multiplet, and br=broad, Mass spectra (MS) were measured with JEOL SX102A GC-MS instrument.

EXAMPLE 1

Mono-[1-(4,8-dioxo-4,8-dihydrobenzo[1,2-b:5,4-b'] dithiophen-2-yl)-methyl]succinate IIa-1

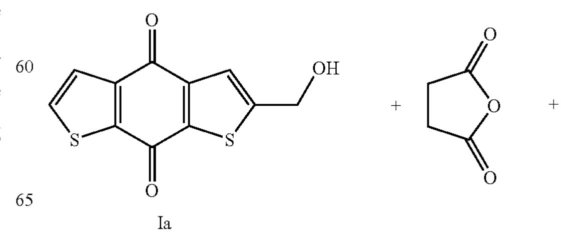

-continued

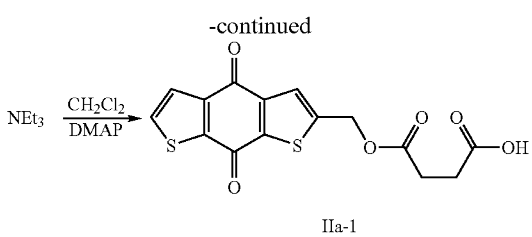

IIa-1

To a stirred solution of Ia (30 mg, 0.12 mmole) in $CH_2Cl_2$ (10 ml) were added succinic anhydride (120 mg, 1.2 mmole), $Et_3N$ (25 mg, 1.23 mmole) and catalytic amount of DMAP (dimethyl aminopyridine). The reaction mixture was stirred at R.T. for 3 hr under $N_2$ and then washed with $H_2O$. The organic layer was extracted with aqueous $NaHCO_3$. To the aqueous layer was added $CH_2Cl_2$ and the pH was adjusted to 1 by 6N HCl. The organic layer was washed with $H_2O$ and the volume was reduced. The solid precipitate was purified by reslurry with diethyl ether to yield yellow solid IIa-1 (13.2 mg, 30%).

$^1H$ NMR (500 MHz, $CDCl_3$) δ 7.67 (d, J=5.0 Hz, 1H), 7.60 (dd, J=6.0, 5.0 Hz, 1H), 7.55 (d, J=6.0 Hz, 1H), 5.32 (s, 2H), 2.70 (s, 4H).

HRMS Calcd for $C_{15}H_{10}O_6S_2$: 349.9919, Found: 350.9995 ($MH^+$, FAB).

mp=156° C. (decomp.)

EXAMPLE 2

Sodium mono-[1-(4,8-dioxo-4,8-dihydrobenzo[1,2-b:5,4-b']dithiophen-2-yl)-methyl]succinate IIa-1-Na

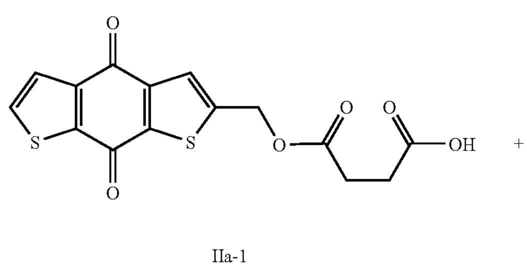

IIa-1

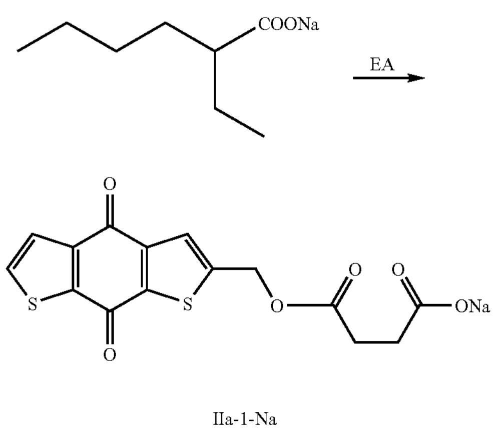

IIa-1-Na

To a stirred solution of IIa-1 (100.7 mg, 0.29 mmole) in EA was added sodium 2-ethylhexanoate (1.2~1.5 eq.) in EA and stirred for overnight. The precipitate was filtered and washed with EA and then dried in vacuum. Yellow solid IIa-1-Na (100.6 mg, 93%) was obtained.

$^1H$ NMR (500 MHz, $CD_3OD$) δ 7.96-7.93 (m, 1H), 7.63-7.60 (m, 2H), 5.36 (s, 2H), 2.63 (t, J=7.0 Hz, 2H), 2.48 (t, J=7.0 Hz, 2H).

mp=213° C. (decomp.)

EXAMPLE 3

Mono-[1-(4,8-dioxo-4,8-dihydrobenzo[1,2-b:5,4-b'] dithiophen-2-yl)-ethyl]succinate IIb-1

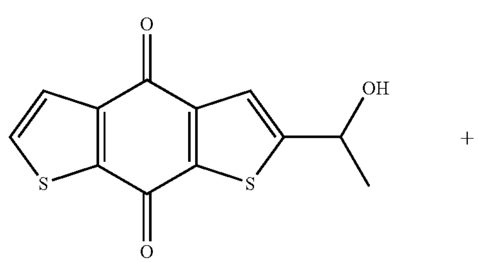

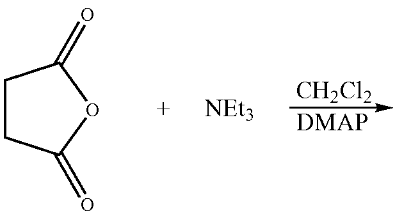

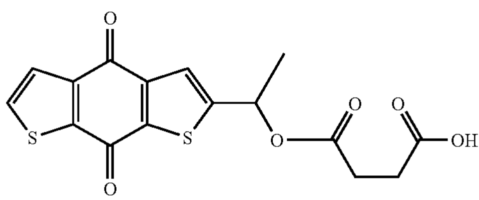

IIb-1

To a stirred solution of Ib (45 mg, 0.18 mmole) and $CH_2Cl_2$ (10 ml) were added succinic anhydride (150 mg, 1.5 mmole), $Et_3N$ (150 mg, 1.54 mmole) and catalytic amount of DMAP (dimethyl aminopyridine). The reaction mixture was stirred at R.T. for 3 hr under $N_2$ and then washed with $H_2O$. The organic layer was extracted with aqueous $NaHCO_3$. To the aqueous layer was added $CH_2Cl_2$, and the pH was adjusted to 1 by 6N HCl. The separated $CH_2Cl_2$ layer was washed with $H_2O$ and the volume was reduced. The solid precipitate was purified by reslurry with diethyl ether to yield yellow solid IIb-1 (11.7 mg, 17%).

$^1H$ NMR (500 MHz, $CDCl_3$) δ 7.66 (d, J=5.0 Hz, 1H), 7.59 (d, J=5.0 Hz, 1H), 7.50 (s, 1H), 6.15 (q, J=6.0 Hz, 1H), 2.71-2.65 (m, 4H), 1.67 (d, J=6.0 Hz, 3H).

HRMS Calcd for $C_{16}H_{12}O_6S_2$: 364.0075, Found: 364.0074.

mp=132~132.5° C.

EXAMPLE 4

Sodium mono-[1-(4,8-dioxo-4,8-dihydroxybenzo-[1,2-b;5,4-b']dithiophen-2-yl)-ethyl]succinate IIb-1-Na

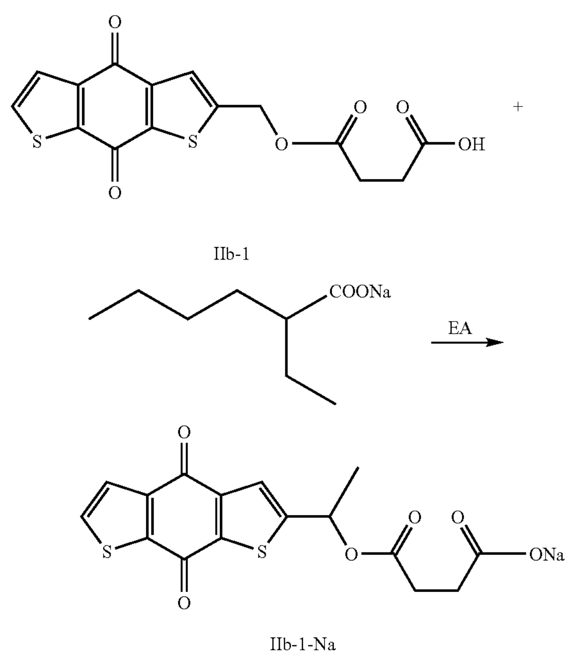

To a stirred solution of IIb-1 (100.8 mg, 0.28 mmole) in EA was added sodium 2-ethylhexanoate (1.2~1.5 eq.) in EA and stirred for overnight. The precipitate was filtered and washed with EA and then dried in vacuum. Yellow solid IIb-1-Na (96.5 mg, 89%) was obtained.

$^1$H NMR (500 MHz, $CD_3OD$) δ 7.94 (d, J=5.0 Hz, 1H), 7.61 (d, J=5.0 Hz, 1H), 7.57 (s, 1H), 6.17 (q, J=6.5 Hz, 1H), 2.68-2.56 (m, 2H), 2.50-2.45 (m, 2H), 1.68 (d, J=6.5 Hz, 3H).

mp=219° C. (decomp.)

EXAMPLE 5

Mono-[1-(4,8-dioxo-4,8-dihydroxybenzo[1,2-b;4,5-b']dithiophen-2-yl)-ethyl]succinate VII-1

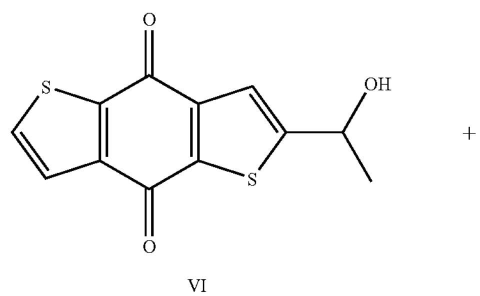

-continued

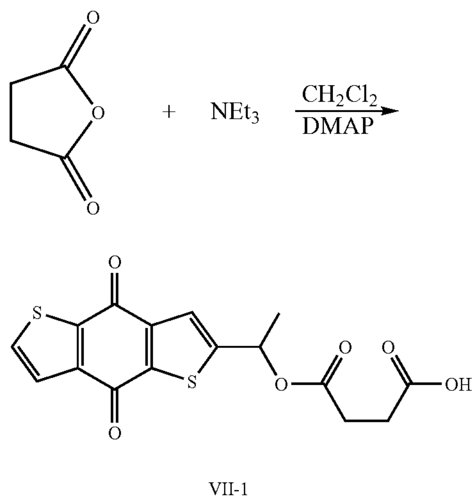

To a stirred solution of VI (50.0 mg, 0.19 mmole) and $CH_2Cl_2$ (3 ml) were added succinic anhydride (44.8 mg, 0.45 mmole), $Et_3N$ (0.10 ml, 0.43 mmole) and DMAP (3.0 mg, 0.02 mmole). The reaction mixture was stirred at R.T. for 1.5 hr under $N_2$. After the addition of $H_2O$ (1 ml) and 6N HCl (1 ml), the reaction mixture was extracted with $CH_2Cl_2$ (15 ml×3). The organic layer was dried over $Na_2SO_4$, filtered and concentrated to yield yellow-green solid VII-1 (62.0 mg, 90%).

$^1$H NMR (500 MHz, $d_6$-DMSO) δ 8.15 (d, J=4.5 Hz, 1H), 7.63 (s, 2H), 6.14 (q, J=6.5 Hz, 1H), 2.59-2.56 (m, 4H), 1.61 (d, J=6.5 Hz, 3H).

HRMS Calcd for $C_{16}H_{12}O_6S_2$: 364.0075, Found: 365.0156 ($MH^+$, FAB).

Mp=163.5~164.6° C.

EXAMPLE 6

Sodium mono-[1-(4,8-dioxo-4,8-dihydroxybenzo-[1,2-b;4,5-b']dithiophen-2-yl)-ethyl]succinate VII-1-Na

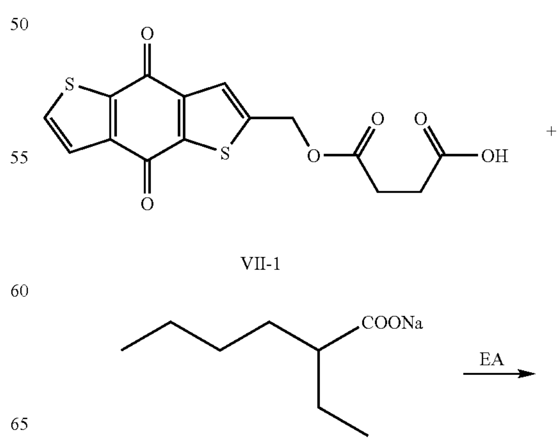

-continued

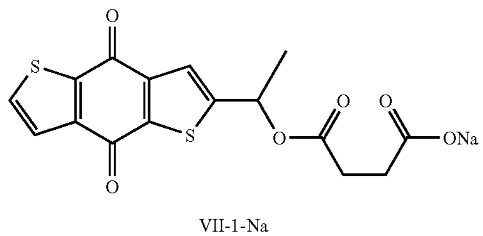

VII-1-Na

To a stirred solution of VII-1 (200.0 mg, 0.55 mmole) in EA was added sodium 2-ethylhexanoate (1.2~1.5 eq.) in EA and stirred for overnight. The precipitate was filtered and washed with EA and then dried in vacuum. Yellow-green solid VII-1-Na (191.0 mg, 90%) was obtained.

$^1$H NMR (500 MHz, CD3OD) δ 7.93 (d, J=5.0 Hz, 1H), 7.62 (d, J=5.0 Hz, 1H), 7.57 (s, 1H), 6.17 (q, J=6.5 Hz, 1H), 2.68-2.56 (m, 2H), 2.49-2.45 (m, 2H), 1.67 (d, J=6.5 Hz, 3H).

mp=240° C. (decomp.)

EXAMPLE 7

Mono-[1-(4,8-dioxo-4,8-dihydrobenzo[1,2-b:5,4-b'] dithiophen-2-yl)-methyl]pentanedioate IIa-2

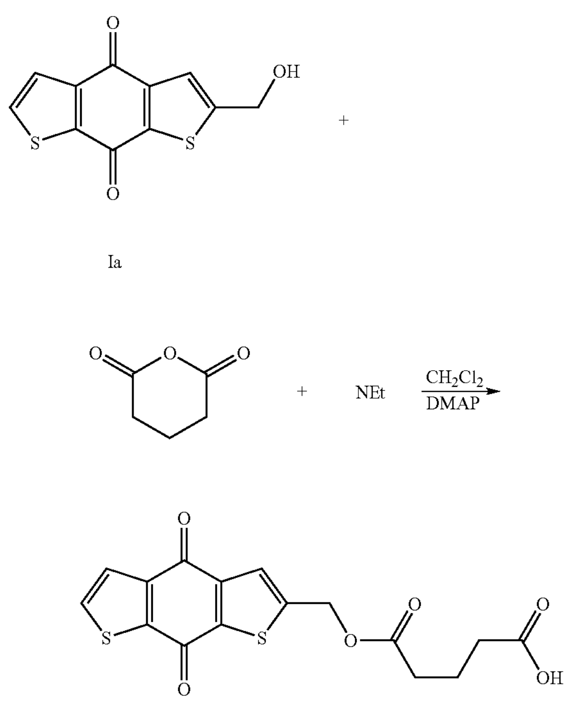

To a stirred solution of Ia (54.0 mg, 0.22 mmole) and $CH_2Cl_2$ (3 ml) were added glutaric anhydride (49.7 mg, 0.44 mmole), DMAP (3.0 mg, 0.02 mmole) and $Et_3N$ (0.06 ml, 0.40 mmole). The reaction mixture was stirred at R.T. for 3.5 hr under $N_2$. After the addition of $H_2O$ (1 ml) and 2N HCl (3 ml), the reaction mixture was extracted with $CH_2Cl_2$ (15 ml×3). The organic layer was dried over $Na_2SO_4$, filtered and concentrated to get crude product. It was purified by column chromatography on silica gel eluting with $CH_3OH$:$CH_2Cl_2$ (1:40) to obtain compound IIa-2 (45.9 mg, 58%).

$^1$H NMR (500 MHz, $CDCl_3$) δ 7.67 (d, J=5.0 Hz, 1H), 7.61 (dd, J=5.5, 5.0 Hz, 1H), 7.55 (d, J=5.5 Hz, 1H), 5.29 (s, 2H), 2.48 (t, J=7.5 Hz, 2H), 2.44 (t, J=7.5 Hz, 2H), 2.02-1.95 (m, 2H).

HRMS Calcd for $C_{16}H_{12}O_6S_2$: 364.0075, Found: 364.0086.

mp=220° C. (decomp.)

EXAMPLE 8

Sodium mono-[1-(4,8-dioxo-4,8-dihydrobenzo[1,2-b:5,4-b']dithiophen-2-yl)methyl]pentanedioate IIa-2-Na

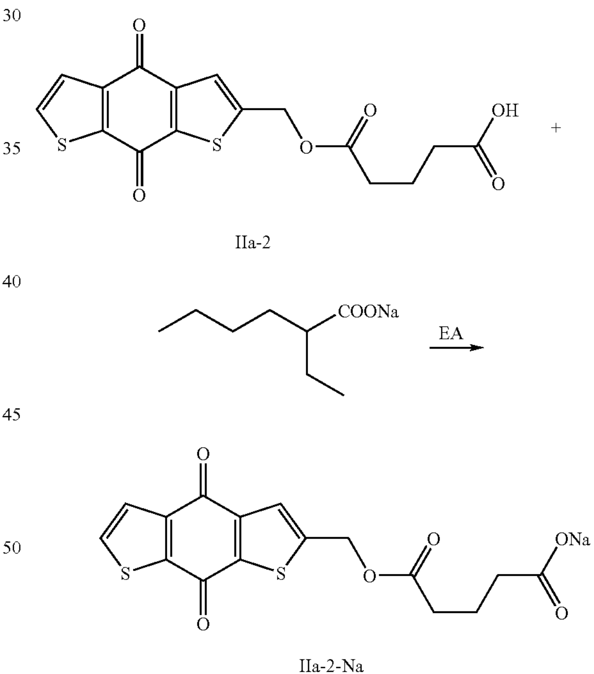

To a stirred solution of IIa-2 (67.1 mg, 0.18 mmole) in EA was added sodium 2-ethylhexanoate (1.2~1.5 eq.) in EA and stirred for overnight. The precipitate was filtered and washed with EA and then dried in vacuum. Yellowish brown solid IIa-2-Na (65.0 mg, 94%) was obtained.

$^1$H NMR (500 MHz, $CD_3OD$) δ 7.97-7.92 (m, 1H), 7.65-7.58 (m, 2H), 5.36 (s, 2H), 2.45 (t, J=7.8 Hz, 2H), 2.21 (t, J=7.8 Hz, 2H), 1.94-1.88 (m, 2H).

mp=203° C. (decomp.)

EXAMPLE 9

Mono-[1-(4,8-dioxo-4,8-dihydrobenzo[1,2-b:5,4-b'] dithiophen-2-yl)-ethyl]pentanedioate IIb-2

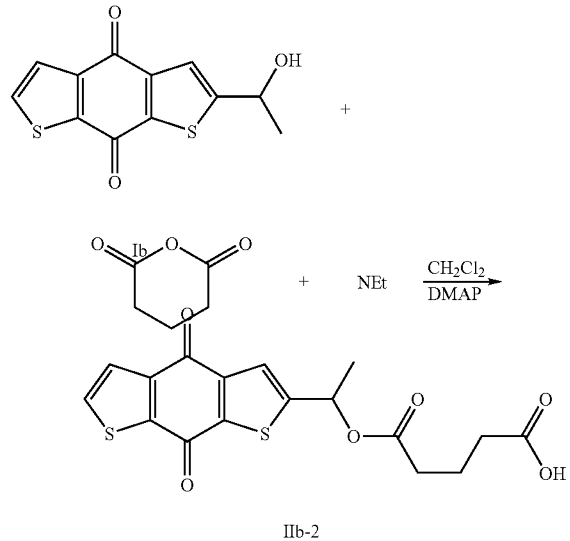

IIb-2

To a stirred solution of Ib (100.0 mg, 0.4 mmole) in $CH_2Cl_2$ (3 ml) were added glutaric anhydride (136.9 mg, 1.2 mmole), DMAP (5.0 mg, 0.04 mmole) and $Et_3N$ (121 mg, 1.19 mmole). The reaction mixture was stirred at R.T. for overnight under $N_2$. After the addition of $H_2O$ (1 ml) and 2N HCl (3 ml), the reaction mixture was extracted with $CH_2Cl_2$ (15 ml×3). The $CH_2Cl_2$ layer was dried over $Na_2SO_4$, filtered and concentrated to get crude product. It was purified by column chromatography on silica gel eluting with $CH_3OH$: $CH_2Cl_2$ (1:40) to obtain compound IIb-2 (128.0 mg, 88%).

$^1$H NMR (500 MHz, $CDCl_3$) δ 7.65 (d, J=5.0 Hz, 1H), 7.59 (d, J=5.0 Hz, 1H), 7.49 (s, 1H), 6.13 (q, J=6.5 Hz, 1H), 2.47-2.40 (m, 4H), 2.00-1.93 (m, 2H, 1.66 (d, J=6.5 Hz, 3H).

HRMS Calcd for $C_{17}H_{14}O_6S_2$: 378.0232, Found: 378.0229.

mp=100.5~101.0° C.

EXAMPLE 10

Sodium mono-[1-(4,8-dioxo-4,8-dihydroxybenzo[1, 2-b;5,4-b']dithiophen-2-yl)-ethyl]pentanedioate IIb-2-Na

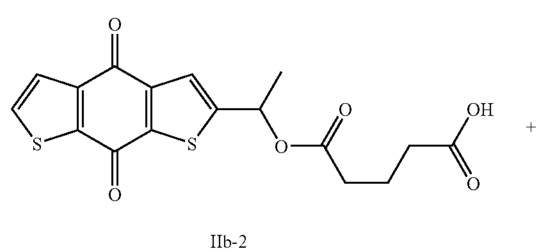

IIb-2

-continued

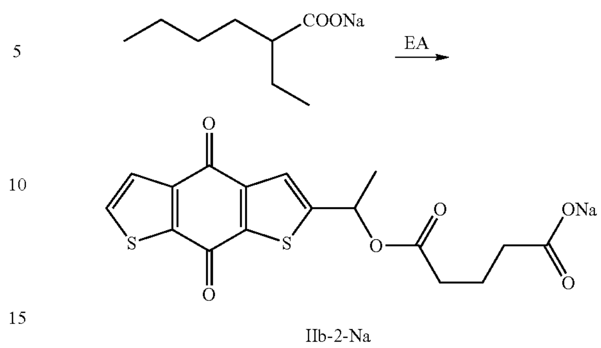

IIb-2-Na

To a stirred solution of IIb-2 (83.0 mg, 0.22 mmole) in EA was added sodium 2-ethylhexanoate (1.2~1.5 eq.) in EA and stirred for overnight. The precipitate was filtered and washed with EA and then dried in vacuum. Yellowish brown solid IIb-2-Na (83.1 mg, 94%) was obtained.

$^1$H NMR (500 MHz, $CD_3OD$) δ 7.94 (d, J=5.0 Hz, 1H), 7.62 (d, J=5.0 Hz, 1H), 7.57 (d, J=1.0 Hz, 1H), 6.18 (dd, J=6.5, 1.0 Hz, 1H), 2.43 (td, J=7.5, 2.5 Hz, 2H), 2.21 (t, J=7.5 Hz, 2H), 1.94-1.88 (m, 2H), 1.67 (d, J=6.5 Hz, 3H).

mp=228° C. (decomp.)

EXAMPLE 11

Mono-[1-(4,8-dioxo-4,8-dihydroxybenzo[1,2-b;4,5-b']dithiophen-2-yl)-ethyl]pentanedioate VII-2

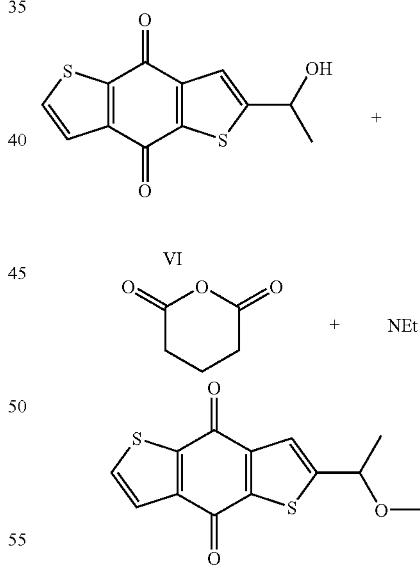

VII-2

To a stirred solution of VI (50.0 mg, 0.19 mmole) in $CH_2Cl_2$ (3 ml) were added glutaric anhydride (45.2 mg, 0.4 mmole), DMAP (3.0 mg, 0.02 mmole) and $Et_3N$ (0.05 ml, 0.4 mmole). The reaction mixture was stirred at R.T. for 15 hr under $N_2$. After the addition of $H_2O$-(1 ml) and 2N HCl (3 ml), the reaction mixture was extracted with $CH_2Cl_2$ (15 ml×3). The $CH_2Cl_2$ layer was dried over $Na_2SO_4$, filtered and concentrated to get crude product. It was purified by column chromatography on silica gel eluting with $CH_3O$: $CH_2Cl_2$ (1:50) to obtain compound VII-2 (32.7 mg, 46%).

$^1$H NMR (500 MHz, $CDCl_3$) δ 7.65 (d, J=5.0 Hz, 1H), 7.61 (d, J=5.0 Hz, 1H), 7.51 (s, 1H), 6.13 (q, J=6.5 Hz, 1H), 2.47-2.41 (m, 4H), 2.00-1.94 (m, 2H 1.66 (d, J=6.5 Hz, 3H).

HRMS Calcd for $C_{17}H_{14}O_6S_2$: 378.0232, Found: 379.0313 ($MH^+$, FAB).

mp=141.6~142.4° C.

EXAMPLE 12

Sodium mono-[1-(4,8-dioxo-4,8-dihydroxybenzo[1, 2-b;4,5-b']dithiophen-2-yl)-ethyl]pentanedioate VII-2-Na

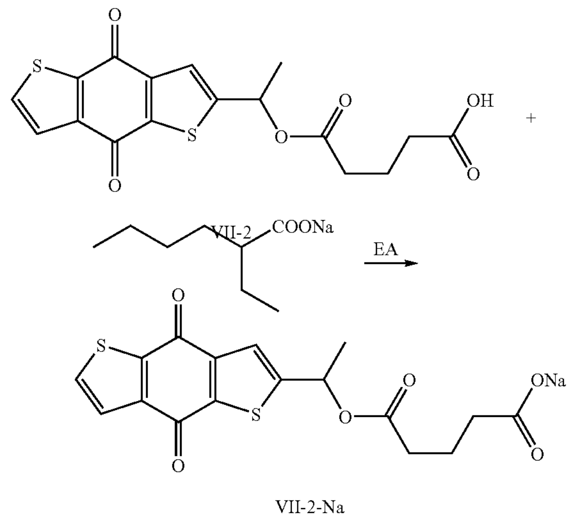

VII-2-Na

To a stirred solution of VII-2 (109.4 mg, 0.29 mmole) in EA was added sodium 2-ethylhexanoate (1.2~1.5 eq.) in EA and stirred for overnight. The precipitate was filtered and washed with EA and then dried in vacuum. Yellow-green solid VII-2-Na (79.0 mg, 68%) was obtained.

$^1$H NMR (500 MHz, $CD_3OD$) δ 7.93 (d, J=5.0 Hz, 1H), 7.62 (d, J=5.0 Hz, 1H), 7.57 (s, 1H), 6.17 (q, J=6.5 Hz, 1H), 2.44 (td, J=7.5, 2.5 Hz, 2H), 2.22 (t, J=7.5 Hz, 2H), 1.95-1.88 (m, 2H), 1.68 (d, J=6.5 Hz, 3H).

mp=230° C. (decomp.)

EXAMPLE 13 t-Butyl 4,8-dioxo-4,8-dihydroxybenzo[1,2-b:5,4-b']-dithiophen-2-yl-methoxy acetate IIIa-1

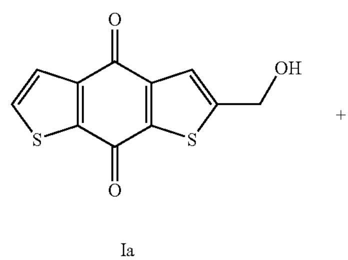
Ia

-continued

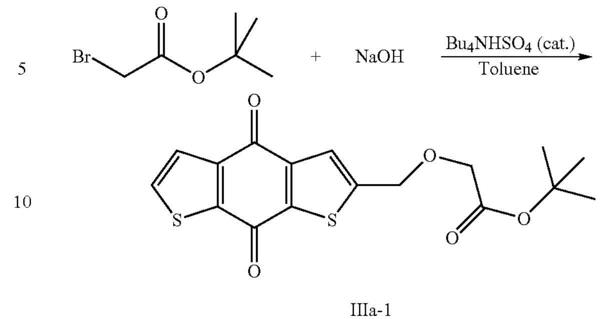

IIIa-1

To a stirred solution of compound Ia (9.4 mg, 0.04 mmole) in toluene (2 ml) were added tetrabutylammonium hydrogen sulfate (4.0 mg, 0.01 mmole), 50% $NaOH_{(aq.)}$ (1 ml) and t-butyl bromoacetate (0.02 ml, 0.1 mmole). The mixture was stirred at R.T. for 2 hr. After the addition of $H_2O$, the reaction mixture was extracted with $CH_2Cl_2$ (15 ml×3). The $CH_2Cl_2$ layer was dried over $Na_2SO_4$, filtered and concentrated to get crude product. It was purified by plate liquid chromatography eluting with Ethyl acetate: Hexane (1:8) to obtain yellow solid IIIa-1 (2.7 mg, 20%).

$^1$H NMR (500 MHz, $CDCl_3$) δ 7.65 (d, J=5.0 Hz, 1H), 7.60 (dd, J=5.5, 5.0 Hz, 1H), 7.49 (d, J=5.5 Hz, 1H), 4.83 (s, 2H), 4.05 (s, 2H), 1.48 (s, 9H).

HRMS Calcd for $C_{17}H_{16}O_5S_2$: 364.0439, Found: 364.0425 mp=97.2~97.8° C.

EXAMPLE 14

Ethyl 4,8-dioxo-4,8-dihydroxybenzo[1,2-b:5,4-b']-dithiophen-2-yl-methoxy acetate IIIa

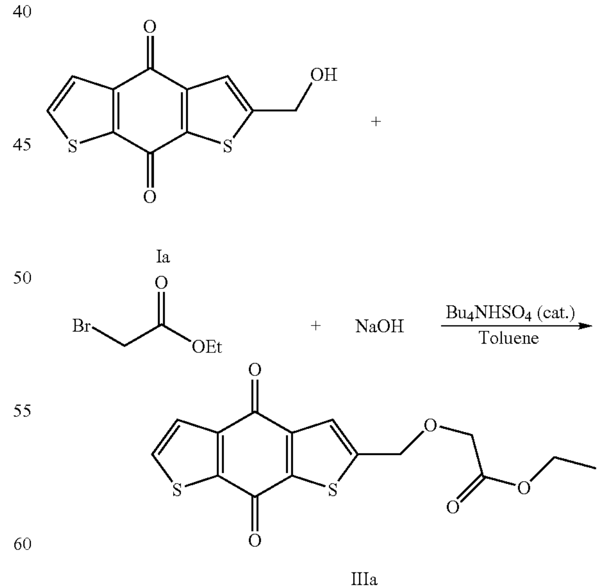

IIIa

To a stirred solution of compound Ia (40 mg, 0.17 mmole) and toluene (10 ml) were added tetrabutylammonium hydrogen sulfate (20 mg, 0.06 mmole), 50% $NaOH_{(aq.)}$ (1 ml) and ethyl bromoacetate (0.1 ml, 0.9 mmole). The mixture was stirred at R.T. for 2 hr. After the addition of $H_2O$, the reaction mixture was extracted with $CH_2Cl_2$ (25 ml×3). The $CH_2Cl_2$ layer was dried over $Na_2SO_4$, filtered and concentrated to get crude product. It was purified by plate liquid chromatography eluting with $CH_2Cl_2$ to obtain yellow solid IIIa (18 mg, 33%).

$^1$H NMR (500 MHz, $CDCl_3$) δ 7.65 (d, J=5.0 Hz, 1H), 7.62-7.59 (m, 1H), 7.51-7.49 (m, 1H), 4.85 (s, 2H), 4.24 (q, J=7.0 Hz, 2H), 4.16 (s, 2H), 1.29 (t, J=7.0 Hz, 3H).

HRMS Calcd for $C_{15}H_{12}O_5S_2$: 336.0126, Found: 336.0125.

mp=113.3~113.5° C.

EXAMPLE 15

4,8-dioxo-4,8-dihydroxybenzo[1,2-b:5,4-b']-dithiophen-2-yl-methoxy acetic acid IVa Method A

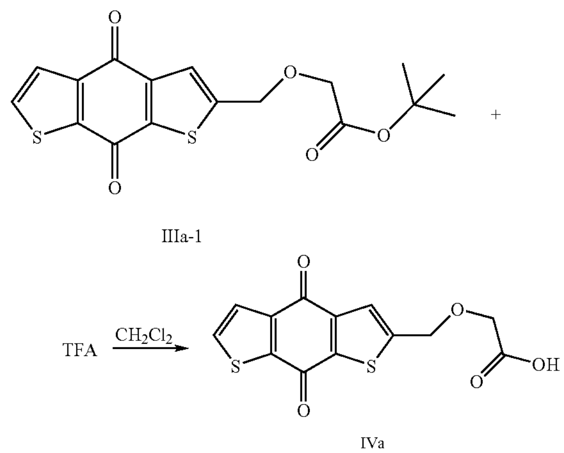

To a stirred solution of compound IIIa-1 (2.7 mg, 0.007 mmole) and $CH_2Cl_2$ (1 ml) was added trifluoroacetic acid (0.1 ml) and stirred at R.T. for 1.5 hr under $N_2$. After concentration, yellow solid IVa was obtained.

Method B

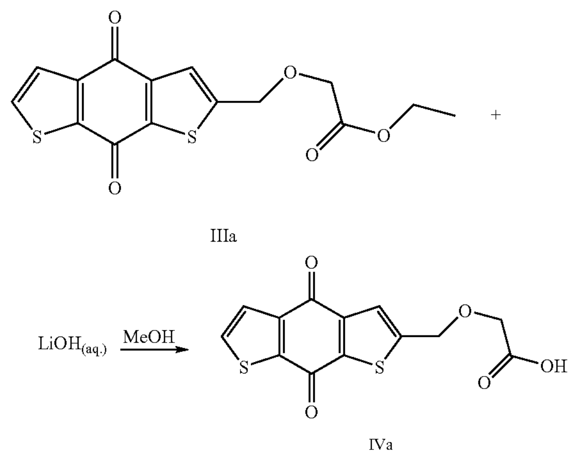

In a 25 mL flask were placed compound IIIa (15 mg, 0.05 mmole) and MeOH (10 ml). LiOH (10 mg) in $H_2O$ (8 ml) was then added and reaction mixture stirred at R.T. until hydrolysis completed. HOAc (~0.4 ml) was added drop-wise to neutralize. MeOH was removed under vacuum and the residue was treated with aq. $Na_2CO_3$ and then extracted with $CH_2Cl_2$. The aqueous layer was acidified with dilute HCl solution until pH~4 and the extracted with $CH_2Cl_2$. The $CH_2Cl_2$ layer was dried with $Na_2SO_4$, filtered and concentrated to obtain yellow solid IVa (12.5 mg, 91%).

$^1$H NMR (500 MHz, $d_6$-DMSO) δ 8.15 (d, J=5.0 Hz, 1H), 7.62 (dd, J=5.0, 4.5 Hz, 1H), 7.57 (d, J=4.5 Hz, 1H), 6.47 (s, 1H), 4.85 (s, 2H), 4.16 (s, 2H).

HRMS Calcd for $C_{13}H_8O_5S_2$: 307.9813, Found: 307.9847.

mp=218.0~218.2° C.

EXAMPLE 16

Sodium 4,8-dioxo-4,8-dihydroxybenzo[1,2-b:5,4-b']-dithiophen-2-yl-methoxy acetate IVa-Na

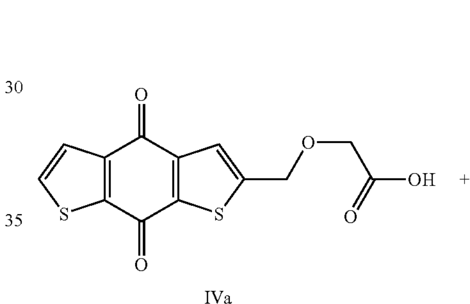

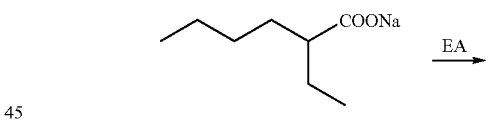

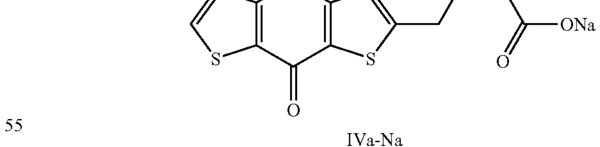

To a stirred solution of IVa (47.8 mg, 0.16 mmole) in EA was added sodium 2-ethylhexanoate (1.2~1.5 eq.) in EA and stirred for overnight. The precipitate was filtered and washed with EA and then dried in vacuum. Yellow-green solid IVa-Na (35.4 mg, 70%).was obtained.

$^1$H NMR (500 MHz, $CD_3OD$) δ 7.93 (br, 1H), 7.62 (br, 1H), 7.54 (s, 1H), 4.88 (s, 2H), 3.97 (s, 2H).

mp=232.7° C. (decomp.)

EXAMPLE 17 t-Butyl 1-(4,8-dioxo-4,8-dihydroxybenzo[1,2-b:5,4-b']-dithiophen-2-yl-ethoxy)-acetate IIIb-1

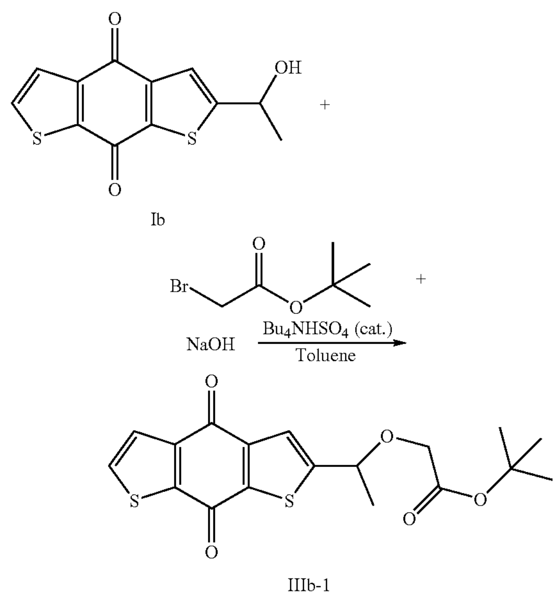

To a stirred solution of compound Ib (9.4 mg, 0.04 mmole) in toluene (2 ml) were added tetrabutylammonium hydrogen sulfate (4.0 mg, 0.01 mmole), 50% $NaOH_{(aq.)}$ (1 ml) and t-butyl bromoacetate (0.02 ml, 0.1 mmole). The mixture was stirred at R.T. for 2 hr. After the addition of $H_2O$, the reaction mixture was extracted with $CH_2Cl_2$ (15 ml×3), and the organic layer was dried over $Na_2SO_4$, filtered and concentrated to get crude product. It was purified by plate liquid chromatography eluting with ethyl acetate: Hexane (1:15) to obtain yellow solid IIIb-1 (6.9 mg, 51%).

$^1$H NMR (500 MHz, $CDCl_3$) δ 7.60 (d, J=5.0 Hz, 1H), 7.595 (d, J=5.0 Hz, 1H), 7.45 (s, 1H), 4.88 (q, J=6.5 Hz, 1H), 4.02, 3.91 (ABq, J=16.5 Hz, 2H), 1.62 (d, J=6.5 Hz, 3H), 1.46 (s, 9H).

HRMS Calcd for $C_{18}H_{18}O_5S_2$: 378.0596, Found, 378.0587 mp=108.0~108.7° C.

EXAMPLE 18

Ethyl 1-(4,8-dioxo-4,8-dihydroxybenzo[1,2-b:5,4-b']-dithiophen-2-yl-ethoxy)-acetate IIIb

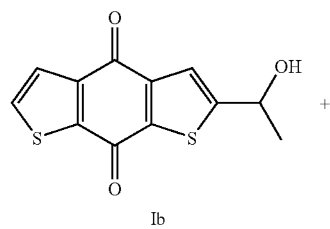

-continued

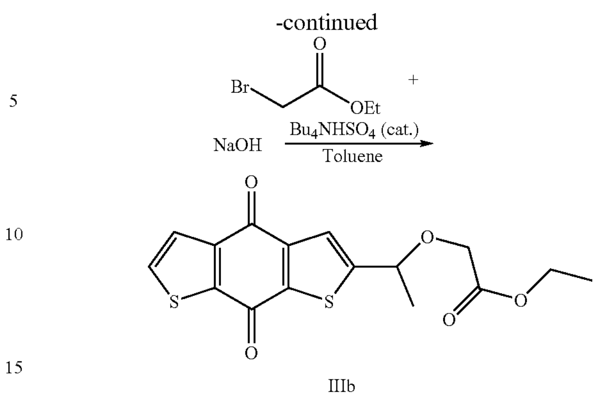

To a stirred solution of compound Ib (100 mg, 0.4 mmole) in toluene (20 ml) were added tetrabutylammonium hydrogen sulfate (40 mg, 0.11 mmole), 50% $NaOH_{(aq.)}$ (1 ml) and ethyl bromoacetate (0.2 ml, 1.8 mmole). The mixture was stirred at R.T. for 2 hr. After the addition of $H_2O$, the reaction mixture was extracted with $CH_2Cl_2$ (20 ml×3). The $CH_2Cl_2$ layer was dried over $Na_2SO_4$, filtered and concentrated to get crude product. It was purified by plate liquid chromatography eluting with $CH_2Cl_2$ to obtain yellow solid. IIIb (65 mg, 48%).

$^1$H NMR (500 MHz, $CDCl_3$) δ 7.65 (d, J=5.0 Hz, 1H), 7.60 (d, J=5.0 Hz, 1H), 7.46 (s, 1H), 4.89 (q, J=6.5 Hz, 1H), 4.21 (q, J=7.0 Hz, 2H), 4.12, 4.02 (ABq, J=16.5 Hz, 2H), 1.63 (d, J=6.5 Hz, 3H), 1.27 (t, J=7.0 Hz, 3H).

HRMS Calcd for $C_{16}H_{14}O_5S_2$: 350.0283, Found: 350.0271.

mp=122.7~122.9° C.

EXAMPLE 19

1-(4,8-Dioxo-4,8-dihydroxybenzo[1,2-b;5,4-b']-dithiophen-2-yl-ethoxy)-acetic acid IVb

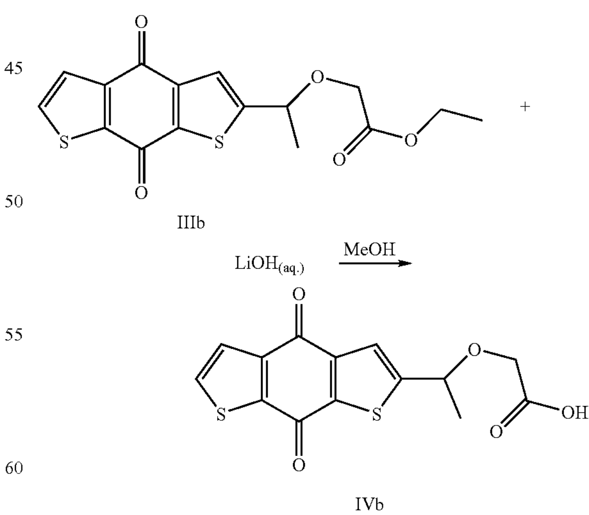

In a 100 mL flask were placed compound IIIb (65 mg, 0.19 mmole) and MeOH (15 ml). LiOH (25.0 mg) in $H_2O$ (12 ml) was then added and reaction mixture stirred at R.T. until hydrolysis completed. HOAc (~1.4 ml) was added drop-wise to neutralize. MeOH was removed under vacuum and the residue was treated with aq. $Na_2CO_3$ and then extracted with $CH_2Cl_2$. The aqueous layer was acidified with dilute HCl solution until pH~4 and the extracted with $CH_2Cl_2$. The $CH_2Cl_2$ layer was dried with $Na_2SO_4$, filtered and concentrated to obtain yellow solid IVb (54 mg, 90%).

$^1$H NMR (500 MHz, $CD_3$ OD) δ 7.95 (d, J=5.0 Hz, 1H), 7.62 (d, J=5.0 Hz, 1H), 7.53 (s, 1H), 4.98 (q, J=6.5 Hz, 1H), 4.15, 4.09 (ABq, J=16.5 Hz, 2H), 1.61 (d, J=6.5 Hz, 3H).

HRMS Calcd for $C_{14}H_{10}O_5S_2$: 321.9970, Found: 321.9994.

mp=172.6~173.0° C.

EXAMPLE 20

Sodium 1-(4,8-dioxo-4,8-dihydroxybenzo[1,2-b:5,4b']-dithiophen-2-yl-ethoxy)-acetate IVb-Na

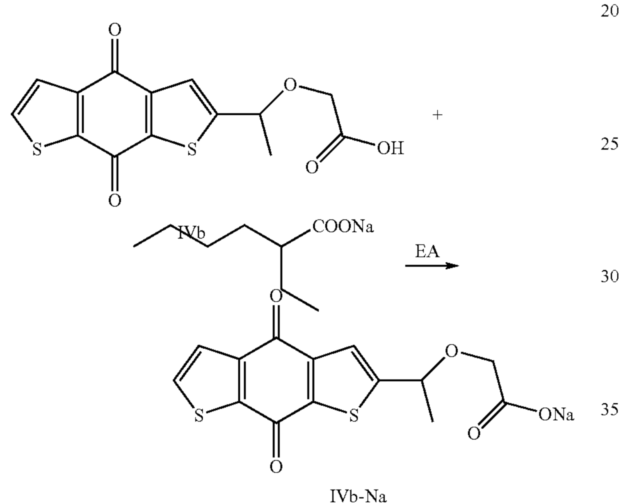

IVb-Na

To a stirred solution of IVb (53.0 mg, 0.16 mmole) in EA was added sodium 2-ethylhexanoate (1.2~1.5 eq.) in EA and stirred for overnight. The precipitate was filtered and washed with EA and then dried in vacuum. Yellow-green solid IVb-Na (33.1 mg, 58%) was obtained.

$^1$H NMR (500 MHz, $D_2O$) δ 7.87 (d, J=5.0 Hz, 1H), 7.32 (d, J=5.0 Hz, 1H), 7.27 (s, 1H), 4.98 (q, J=6.5 Hz, 1H), 4.02, 3.94 (ABq, J=16.0 Hz, 2H), 1.64 (d, J=6.5 Hz, 3H).

mp=243.8~244.2° C.

EXAMPLE 21 t-Butyl 1-(4,8-dioxo-4,8-dihydroxybenzo[1,2-b:4,5-b']-dithiophen-2-yl-ethoxy)acetate VIII-1

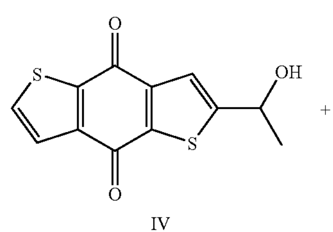

IV

-continued

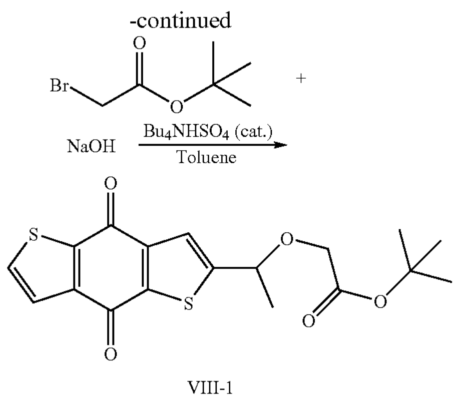

VIII-1

To a stirred solution of compound VI (9.0 mg, 0.03 mmole) in toluene (2 ml) were added tetrabutylammonium hydrogen sulfate (4.0 mg, 0.01 mmole), 50% $NaOH_{(aq.)}$ (1 ml) and t-butyl bromoacetate (0.02 ml, 0.1 mmole). The mixture was stirred at R.T. for 2 hr. After the addition of $H_2O$, the reaction mixture was extracted with $CH_2Cl_2$ (15 ml×3), and the organic layer was dried over $Na_2SO_4$, filtered and concentrated to get crude product. It was purified by plate liquid chromatography eluting with ethyl acetate: Hexane (1:15) to obtain yellow oil VIII-1 (5.0 mg, 39%).

$^1$H NMR (500 MHz, $CDCl_3$) δ 7.65 (d, J=5.0 Hz, 1H), 7.61 (d, J=5.0 Hz, 1H), 7.46 (s, 1H), 4.87 (q, J=6.5 Hz, 1H), 4.01, 3.90 (ABq, J=16.5 Hz, 2H), 1.62 (d, J=6.5 Hz, 3H), 1.46 (s, 9H).

HRMS Calcd for $C_{18}H_{18}O_5S_2$: 378.0596, Found: 378.0573

EXAMPLE 22

Ethyl 1-(4,8-dioxo-4,8-dihydroxybenzo[1,2-b:4,5-b']-dithiophen-2-yl-ethoxy)acetate VIII

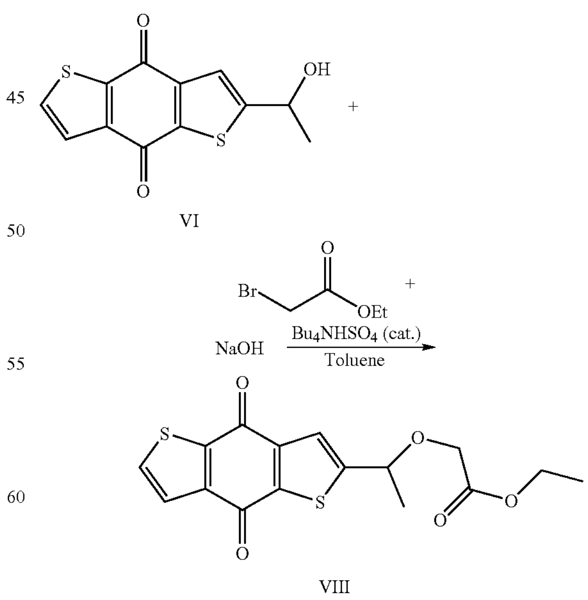

To a stirred solution of compound VI (9.7 mg, 0.04 mmole) and toluene (2 ml) were added tetrabutylammonium hydrogen sulfate (4.0 mg, 0.01 mmole), 50% $NaOH_{(aq.)}$ (1 ml) and ethyl bromoacetate (0.1 mmole). The mixture was stirred at R.T. for 2 hr. After the addition of $H_2O$, the reaction mixture was extracted with $CH_2Cl_2$ (15 ml×3). The $CH_2Cl_2$ layer was dried over $Na_2SO_4$, filtered and concentrated to get crude product. It was purified by plate liquid chromatography eluting with $CH_2Cl_2$ to obtain yellow solid VIII (2.5 mg, 19%).

$^1H$ NMR (500 MHz, $CDCl_3$) δ 7.65 (d, J=5.0 Hz, 1H), 7.61 (d, J=5.0 Hz, 1H), 7.47 (s, 1H), 4.89 (q, J=6.5 Hz, 1H), 4.21 (q, J=7.0 Hz, 2H), 4.12, 4.02 (ABq, J=16.5 Hz, 2H), 1.63 (d, J=6.5 Hz, 3H), 1.27 (t, J=7.0 Hz, 3H).

HRMS Calcd for $C_{16}H_{14}O_5S_2$: 350.0283, Found: 350.0284.

mp=106.2~107.1° C.

EXAMPLE 23

1-(4,8-Dioxo-4,8-dihydroxybenzo[1,2-b:4,5-b']-dithiophen-2-yl-ethoxy)-acetic acid IX

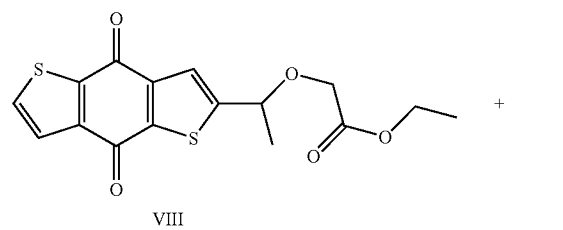

VIII

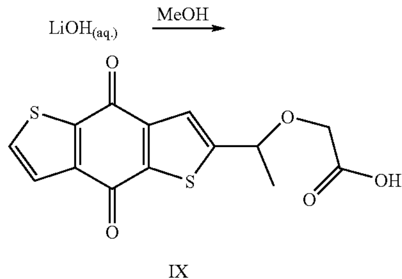

IX

In a 25 mL flask were placed compound VIII (192.7 mg, 0.55 mmole) and MeOH (30 ml). LiOH (0.36 g) in $H_2O$ (30 ml) was then added and reaction mixture stirred at R.T. until hydrolysis completed. HOAc (~1.1 ml) was added dropwise to neutralize. MeOH was removed under vacuum and the residue was treated with aq. $Na_2CO_3$ and then extracted with EA. The aqueous layer was acidified with dilute HCl solution until pH~4 and the extracted with EA. The EA layer was dried with $Na_2SO_4$, filtered and concentrated to obtain yellow solid IX (160.0 mg, 90%).

$^1H$ NMR (500 MHz, $CD_3OD$) δ 7.90 (d, J=5.0 Hz, 1H), 7.60 (d, J=5.0 Hz, 1H), 7.51 (s, 1H), 4.96 (q, J=6.5 Hz, 1H), 4.15, 4.09 (ABq, J=16.5 Hz, 2H), 1.61 (d, J=6.5 Hz, 3H).

HRMS Calcd for $C_{14}H_{10}O_5S_2$: 321.9970, Found: 323.0054 ($MH^+$, FAB).

mp=172.1~172.8° C.

EXAMPLE 24

Sodium 1-(4,8-dioxo-4,8-dihydroxybenzo[1,2-b:4,5-b']-dithiophen-2-yl-ethoxy)-acetate IX-Na

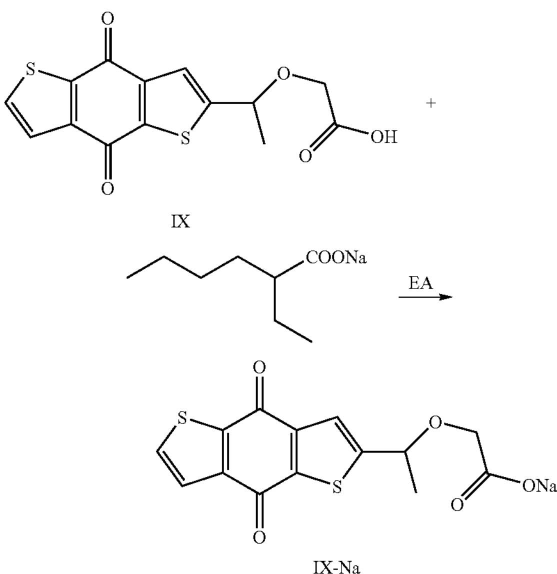

To a stirred solution of IX (85.0 mg, 0.28 mmole) in EA was added sodium 2-ethylhexanoate (1.2~1.5 eq.) in EA and stirred for overnight, The precipitate was filtered and washed with EA and then dried in vacuum. Yellow solid IX-Na (83.0 mg, 92%) was obtained.

$^1H$ NMR (500 MHz, $CD_3OD$) δ 7.92 (d, J=5.0 Hz, 1H), 7.62 (d, J=5.0 Hz, 1H), 7.52 (s, 1H), 4.96 (q, J=6.5 Hz, 1H), 3.92, 3.83 (ABq, J=15.5 Hz, 2H), 1.60 (d, J=6.5 Hz, 3H).

mp=223° C. (decomp.)

EXAMPLE 25

2-[1-(2-Pyrrol-1-yl-propoxy)-ethylbenzo[1,2-b:4,5-b']dithiophen-4,8-dione X

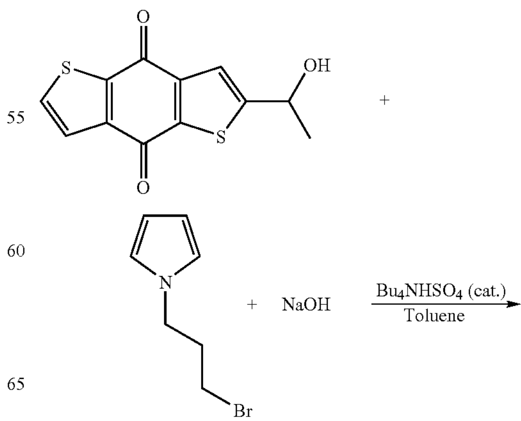

-continued

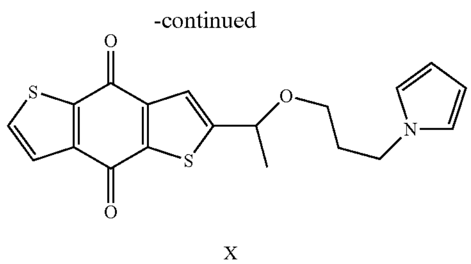

X

To a stirred solution of compound VI (10.5 mg, 0.04 mmole) in toluene (2 ml) were added tetrabutylammonium hydrogen sulfate (4.0 mg, 0.01 mmole), 50% $NaOH_{(aq.)}$ (2 ml) and 1-(3-bromopropyl)pyrrole (0.1 mmole). The mixture was stirred at R.T. for 3 hr. After the addition of $H_2O$, the reaction mixture was extracted with $CH_2Cl_2$ (15 ml×3). The $CH_2Cl_2$ layer was dried over $Na_2SO_4$, filtered and concentrated to get crude product. It was purified by plate liquid chromatography eluting with $CH_2Cl_2$ to obtain yellow oil X (5.0 mg, 34%).

$^1$H NMR (500 MHz, $CDCl_3$) δ 7.65 (d, J=5.0 Hz, 1H), 7.61 (d, J=5.0 Hz, 1H), 7.41 (s, 1H), 6.61 (s, 2H), 6.10 (s, 2H), 4.64 (q, J=6.5 Hz; 1H), 4.06-3.94 (m, 2H), 3.38 (t, J=5.5 Hz, 2H), 2.04-1.99 (m, 2H), 1.56 (d, J=6.5 Hz, 3H).

HRMS Calcd for $C_{19}H_{17}NO_3S_2$: 371.0650, Found: 371.0663

EXAMPLE 26

4,8-dioxo-4,8-dihydrobenzo[1,2-b;5,4-b'] dithiophene-2-carboxylate-(2-dimethylamino-ethyl)-amide XVII

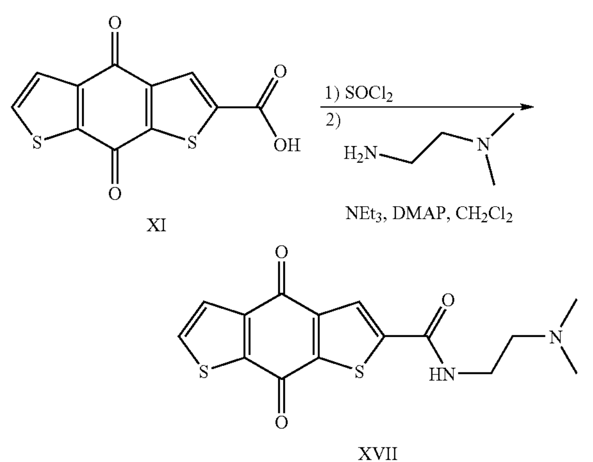

Compound XI (60 mg, 0.23 mmole) in $SOCl_2$ (5 ml) was heated to reflux for 2 hrs. The excess $SOCl_2$ was removed to yield crude acid chloride. The acid chloride obtained was used directly without purification. It was diluted with $CH_2Cl_2$ (4 ml) and added to the N,N-dimethylethylenediamine (1.5 ml), $Et_3N$ (2 ml) and $CH_2Cl_2$ (4 ml) mixture and stirred at R.T. for 1.5~2 hrs. Water was added and the reaction mixture extracted with $CH_2Cl_2$, The $CH_2Cl_2$ layer was concentrated and crude product was purified through column using MeOH: $CH_2Cl_2$=1:8 as the eluent. Yellow solid XVII (50.0 mg, 67%) was obtained.

$^1$H NMR (500 MHz, $CD_3OD$) δ 8.14 (d, J=2.0 Hz, 1H), 7.97~8.00 (m, 1H), 7.65 (d, J=5.0 Hz, 1H), 3.54 (t, J=6.5 Hz, 2H), 2.59 (t, J=6.5 Hz, 2H), 2.33 (s, 6H).

HRMS Calcd for $C_{15}H_{14}N_2O_3S_2$: 334.0446, Found: 334.0435 mp=197.5~198.0° C.

EXAMPLE 27

4,8dioxo-4,8-dihydrobenzo[1,2-b;5,4-b']dithiophene-2-carboxylate-(2-dimethyl-aminoethyl)-amide phosphoric acid salt XVII-$H_3PO_4$

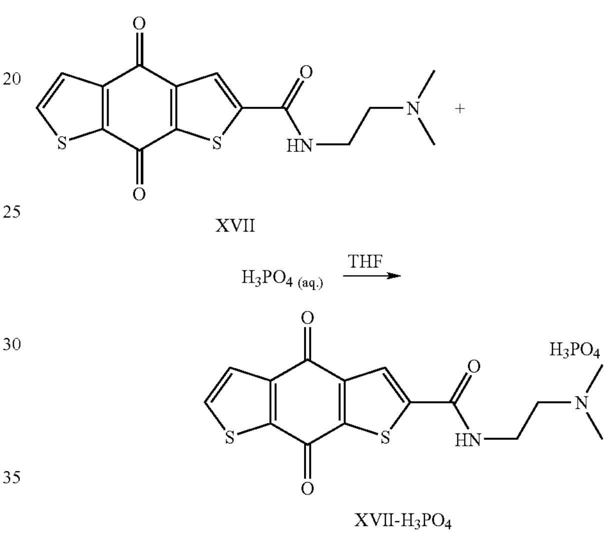

To a stirred solution of XVII (31 mg, 0,093 mmole) in THF was added 85% $H_3PO_4$ (1.2~1.5 eq.) and stirred for overnight. The precipitate was filtered and washed with THF and then dried in vacuum. Yellow solid XVII-$H_3PO_4$ (39 mg, 97%) was obtained.

$^1$H NMR (500 MHz, $D_2O$) δ 8.16 (s, 1H), 8.02 (d, J=5.0 Hz, 1H), 7.66 (d, J=5.0 Hz, 1H), 3.78 (t, J=6.0 Hz, 2H), 3.37 (t, J=6.0 Hz, 2H), 2.97 (s, 6H).

mp=222.5° C. (decomp.)

EXAMPLE 28

(a) Ammonium 4,8-dioxo-4,8-dihydrobenzo-[1,2-b:5,4-b']dithiophene-2-carboxylate XI-$NH_4$

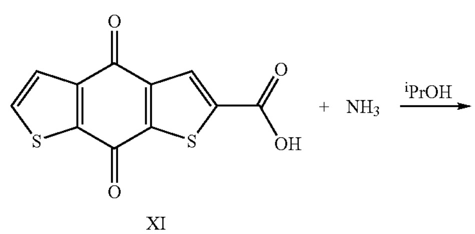

-continued

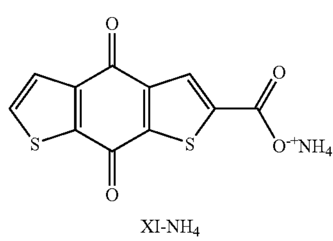
XI-NH4

Aqueous ammonium hydroxide (29.5%) was added to the solution of compound XI (230 mg, 0.87 mmole) in IPA (40 mL) until basic. After stirring for a while, all the volatile solvent was removed to yield green-yellow solid XI-$NH_4$ (200 mg, 82%)

$^1$H NMR (500 MHz, $CD_3OD$) δ 7.94 (d, J=5.0 Hz, 1H), 7.91 (s, 1H), 7.62 (d, J=5.0 Hz, 1H).

mp=257~259° C.

(b) Sodium 4,8-dioxo-4,8-dihydrobenzo-[1,2-b:5,4-b']dithiophene-2 carboxylate XI-Na

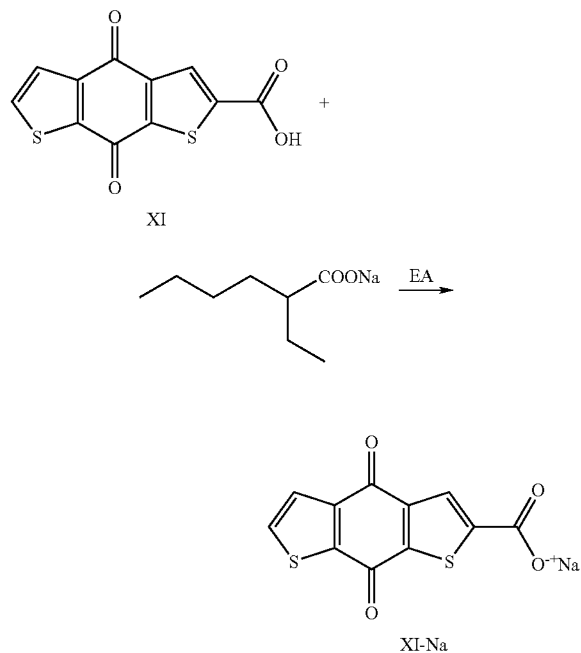
XI-Na

To a stirred solution of XI (206.7 mg, 0.83 mmole) in EA was added sodium 2-ethylhexanoate (1.2~1.5 eq.) in EA and stirred for overnight. The precipitate was filtered and washed with EA and then dried in vacuum. Yellowish brown solid XI-Na (202.5 mg, 90%) was obtained.

1H NMR (500 MHz, $CD_3OD$) δ 7.93 (dd, J=5.0, 2.0 Hz, 1H), 7.90 (d, J=2.0 Hz, 1H), 7.62 (d, J=5.0 Hz, 1H).

mp=>275° C. (decomp.)

EXAMPLE 29

(2S)-[(4,8-Dioxo-4,8-dihydroxybenzo[1,2-b:5,4-b']dithiophen-2-carbonyl)-amino]-phenyl-acetic acid methyl ester XII-1

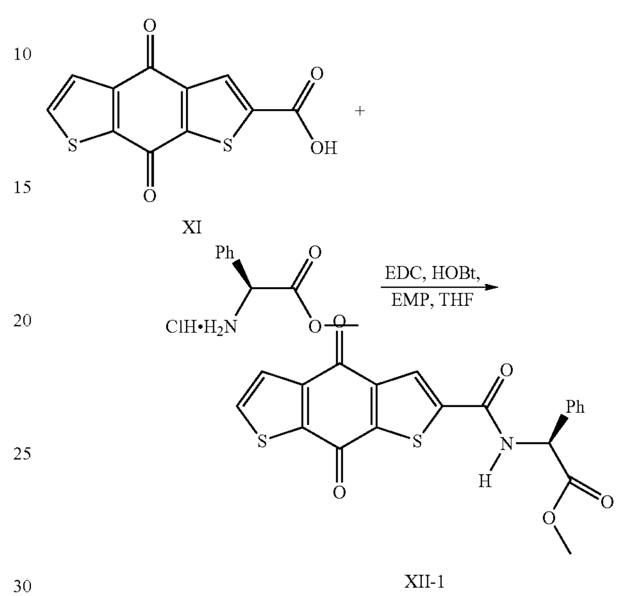
XII-1

To a stirred solution of XI (40.0 mg, 0.15 mmole) and THF (2 ml) were added (S)-phenyl glycine methyl ester HCl salt (31 mg, 0.15 mmole), EDC (30.5 mg, 0.16 mmole), HOBt (21 mg, 0.15 mmole) and 4-ethylmorpholine (0.02 ml, 0.15 mmole). After stirring at R.T. for overnight under $N_2$, the solvent was removed under reduced pressure. $CH_2Cl_2$ (3 ml) was added to the residue and the insoluble solid was removed. The $CH_2Cl_2$ layer was then washed with saturated $NaHCO_3$ solution, 1M $KHSO_4$, saturated $NaHCO_3$ solution and $H_2O$. The organic layer was dried over $Na_2SO_4$, filtered and concentrated to get crude product. It was purified by column chromatography on silica gel eluting with EA: Hexanes (1:3) to obtain yellow solid XII-1 (21.1 mg, 34%).

$^1$H NMR (500 MHz, $CDCl_3$) δ 7.95 (s, 1H), 7.71 (d, J=4.3 Hz, 1H), 7.64 (d, J=4.3 Hz, 1H), 7.41-7.30 (m, 5H), 7.16 (d, J=6.5 Hz, 1H), 5.71 (d, J=6.5 Hz, 1H), 3.78 (s, 3H).

HRMS Calcd for $C_{20}H_{13}NO_5S_2$: 411,0235, Found: 411.0229 mp=211.1~211.9° C.

EXAMPLE 30

[(4,8-Dioxo-4,8-dihydroxybenzo[1,2-b;5,4-b']dithiophen-2-carbonyl)-amino]-acetic acid isopropyl ester XII-2

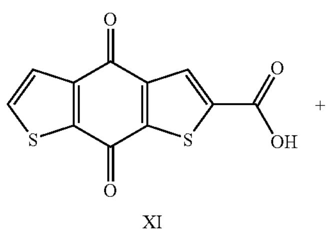
XI

-continued

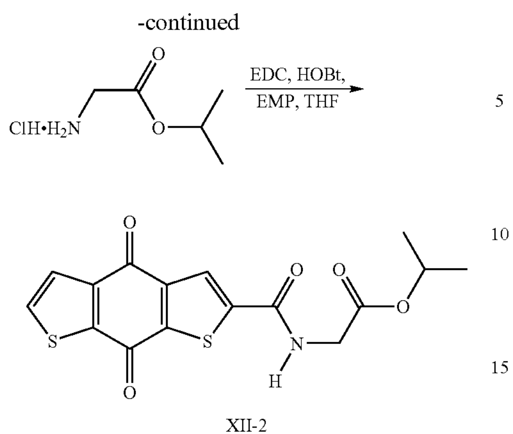

To a stirred solution of XI (52.6 mg, 0.20 mmole) and THF (2 ml) were added isopropyl glycinate HCl salt (30.4 mg, 0.21 mmole), EDC (40.1 mg, 0.21 mmole), HOBt (27.0 mg, 0.21 mmole) and 4-ethylmorpholine (0.03 ml, 0.21 mmole). After stirring at R.T. for overnight under $N_2$, the solvent was removed under reduced pressure. $CH_2Cl_2$ (3 ml) was added to the residue and the insoluble solid was removed. The $CH_2Cl_2$ layer was then washed with saturated $NaHCO_3$ solution, 1M $KHSO_4$, saturated $NaHCO_3$ solution and $H_2O$. The organic layer was dried over $Na_2SO_4$, filtered and concentrated to get crude product. It was purified by column chromatography on silica gel eluting with EA: $CH_2Cl_2$ (1:20) to obtain yellow solid XII-2 (31.7 mg, 44%).

$^1$H NMR (500 MHz, $CDCl_3$) δ 7.94 (s, 1H), 7.71 (d, J=4.5 Hz, 1H), 7.63 (d, J=4.5 Hz, 1H), 6.73 (s, 1H), 5.12 (septet, J=6.5 Hz, 1H), 4.18 (d, J=4.5 Hz, 2H), 1.29 (d, J=6.5 Hz, 6H).

HRMS Calcd for $C_{16}H_{13}NO_5S_2$: 363.0235, Found: 363.0226 mp=240.2~240.5° C.

EXAMPLE 31

(2S)-[(4,8-Dioxo-4,8-dihydroxybenzo[1,2-b;4,5b'] dithiophen-2-carbonyl)-amino]-propionic acid methyl ester XII

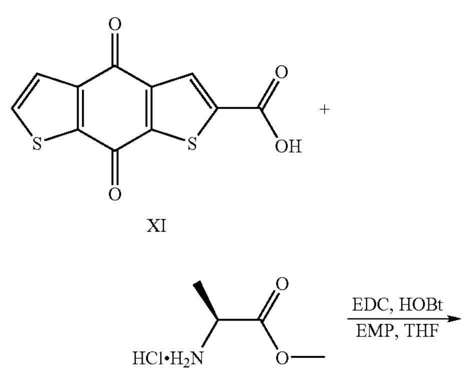

-continued

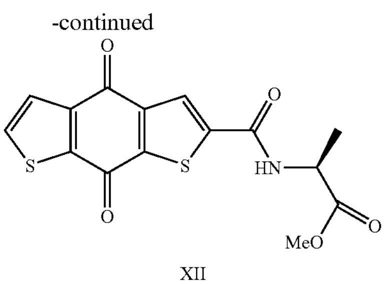

To a stirred solution of XI (40.0 mg, 0.15 mmole) and THF (2 ml) were added (S)-alanine methyl ester HCl salt (21 mg, 0.15 mmole), EDC (30.5 mg, 0.16 mmole), HOBt (21 mg, 0.15 mmole) and 4-ethylmorpholine (0.02 ml, 0.15 mmole). After stirring at R.T. for overnight under $N_2$, the solvent was removed under reduced pressure. $CH_2Cl_2$ (3 ml) was added to the residue and the insoluble solid was removed. The $CH_2Cl_2$ layer was then washed with saturated $NaHCO_3$ solution, 1M $KHSO_4$, saturated $NaHCO_3$ solution and $H_2O$. The organic layer was dried over $Na_2SO_4$, filtered and concentrated to get crude product. It was purified by column chromatography on silica gel eluting with EA: Hexanes (1:2) to obtain yellow solid XII (27.5 mg, 52%).

$^1$H NMR (500 MHz, $CDCl_3$) δ 7.92 (s, 1H), 7.72 (d, J=5.0 Hz, 1H), 7.64 (d, J=5.0 Hz, 1H), 6.75 (d, J=6.5 Hz, 1H), 4.78-4.72 (m, 1H), 3.80 (s, 3H), 1.54 (d, J=7.0 Hz, 3H).

HRMS Calcd for $C_{15}H_{11}NO_5S_2$: 349.0079, Found: 349.0061.

mp=188.1~188.6° C.

EXAMPLE 32

(L)-2-{(4,8-Dioxo-4,8-dihydrobenzo-[1,2-b;5,4-b'] dithiophene-2-carbonyl)-amino}-propionic acid XIII

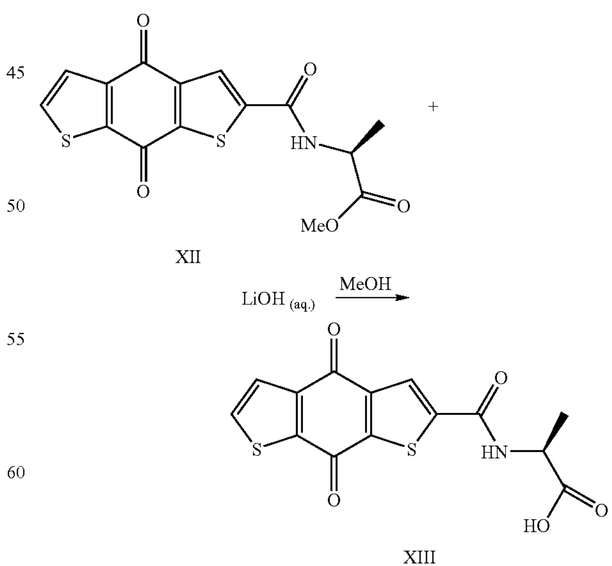

In a 25 mL flask were placed compound XII (130 mg, 0.37 mmole) and MeOH (37 ml), LiOH (322.5 mg) in $H_2O$ (30 ml) was then added and reaction mixture stirred at R.T. until hydrolysis completed. HOAc (~1.0 ml) was added dropwise to neutralize. MeOH was removed under vacuum and the residue was treated with aq. $Na_2CO_3$ and then extracted with EA. The aqueous layer was acidified with dilute HCl solution until pH~4 and the extracted with EA. The EA layer was dried with $Na_2SO_4$, filtered and concentrated to obtain yellow solid XIII (120 mg, 96%).

$^1$H NMR (500 MHz, $CD_3OD$) δ 8.25 (s, 1H), 8.00 (d, J=5.0 Hz, 1H), 7.66 (d, J=5.0 Hz, 1H), 4.58 (q, J=7.5 Hz, 1H), 1.53 (d, J=7.5 Hz, 3H).

HRMS Calcd for $C_{14}H_9NO_5S_2$: 334.9922, Found; 334.9931 mp=239° C. (decomp.)

EXAMPLE 33

Sodium (L)-2-{(4,8-dioxo-4,8-dihydrobenzo-[1,2-b;5,4-b']dithiophene-2-carbonyl)-amino}-propionate XIII-Na

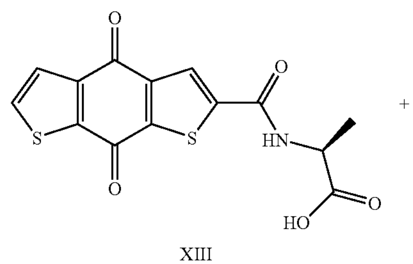

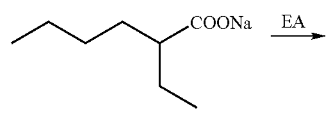

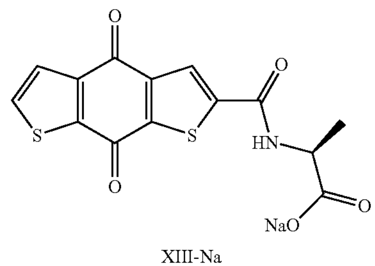

To a stirred solution of XIII (50.5 mg, 0.15 mmole) in EA was added sodium 2-ethylhexanoate (1.2~1.5 eq.) in EA and stirred for overnight. The precipitate was filtered and washed with EA and then dried in vacuum. Yellow solid XIII-Na (27.8 mg, 52%) was obtained.

$^1$H NMR (50 MHz, $D_2O$) δ 7.93 (br, 1H), 7.80 (d, J=5.0 Hz, 1H), 7.44 (d, J=5.0 Hz, 1H), 4.31 (q, J=6.5 Hz, 1H), 1.50 (d, J=6.5 Hz, 3H).

mp=200.5° C. (decomp.)

EXAMPLE 34

Ammonium 4,8-dioxo-4,8-dihydrobenzo-[1,2-b;4,5-b']dithiophene-2-carboxylate XIV-$NH_4$

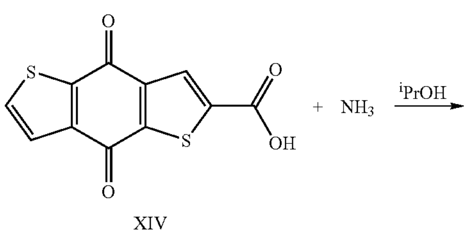

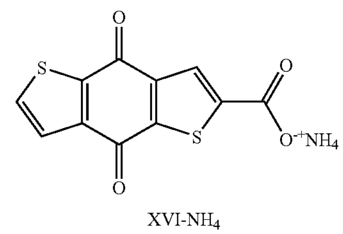

Compound XIV (140 mg, 0.53 mmole) was added in IPA (20 mL) and stirred at 60° C. for 30 min. The solid that was not soluble in IPA was filtered. Aqueous ammonium hydroxide (29.5%) was added to the filtrate until basic. After stirring for a while, the solvent was evaporated to yield green-yellow solid XIV-$NH_4$ (68.5 mg, 46%)

$^1$H NMR (500 MHz, $CD_3OD$) δ 7.97 (s, 1H), 7.94 (d, J=5.0 Hz, 1H), 7.64 (d, J=5.0 Hz, 1H).

mp>300° C.

EXAMPLE 35

[(4,8-Dioxo-4,8-dihydroxybenzo[1,2-b;4,5-b']dithiophen-2-carbonyl)-amino]-acetic acid isopropyl ester XV

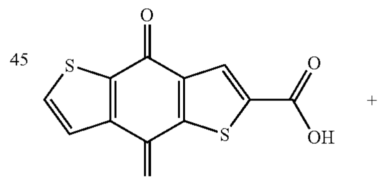

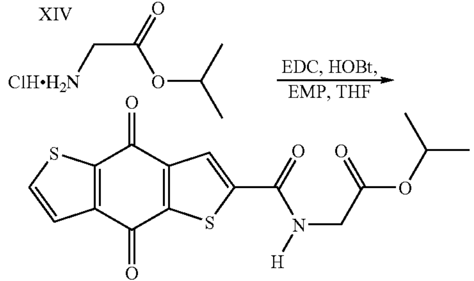

To a stirred solution of XIV (244.6 mg, 0.90 mmole) and THF (8 ml) were added isopropyl glycinate HCl salt (140.0 mg, 0.92 mmole), EDC (190.0 mg, 0.99 mmole), HOBt (125.0 mg, 0.93 mmole) and 4-ethylmorpholine (0.12 ml, 0.80 mmole). After stirring at R.T. for overnight under $N_2$, the solvent was removed under reduced pressure. $CH_2Cl_2$ (12 ml) was added to the residue and the insoluble solid was removed. The $CH_2Cl_2$ layer was then washed with saturated $NaHCO_3$ solution, 1M $KHSO_4$, saturated $NaHCO_3$ solution and $H_2O$. The organic layer was dried over $Na_2SO_4$, filtered and concentrated to get crude product. It was purified by column chromatography on silica gel eluting with EA: $CH_2Cl_2$ (1:30) to obtain yellow solid XV (75.1 mg, 21%).

$^1$H NMR (500 MHz, $CDCl_3$) δ 7.95 (s, 1H), 7.70 (d, J=5.0 Hz, 1H), 7.65 (d, J=5.0 Hz, 1H), 6.73 (t, J=4.5 Hz, 1H), 5.12 (septet, J=6.5 Hz, 1H), 4.18 (d, J=4.5 Hz, 2H), 1.29 (d, J=6.5 Hz, 6H).

HRMS Calcd for $C_{16}H_{13}NO_5S_2$: 363.0235, Found: 363.0228 mp=231.8~233.0° C.

EXAMPLE 36

Methyl (L)-2-{(4,8-Dioxo-4,8-dihydrobenzo-[1,2-b:4,5-b']dithiophene-2-carbonyl)-amino}propionate XV-1

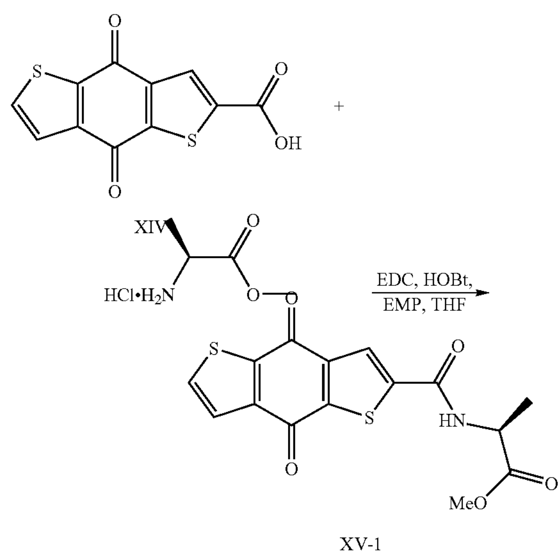

To a stirred solution of XIV (79.8 mg, 0.30 mmole) in THF (10 ml) were added (S)-alanine methyl ester HCl salt (42.0 mg, 0.30 mmole), EDC (61.0 mg, 0.32 mmole), HOBt (42 mg, 0.30 mmole) and 4-ethylmorpholine (0.04 ml, 0.30 mmole). After stirring at R.T. for overnight under $N_2$, the solvent was removed under reduced pressure. $CH_2Cl_2$ (3 ml) was added to the residue and the insoluble solid was removed. The $CH_2Cl_2$ layer was then washed with saturated $NaHCO_3$ solution, 1M $KHSO_4$, saturated $NaHCO_3$ solution and $H_2O$. The organic layer was dried over $Na_2SO_4$, filtered and concentrated to get crude product. It was purified by column chromatography on silica gel eluting with EA: Hexanes (1:2) to obtain yellow solid XV-1 (38.1 mg, 36%).

$^1$H NMR (500 MHz, $CDCl_3$) δ 7.94 (s, 1H), 7.71 (d, J=5.0 Hz, 1H), 7.65 (d, J=5.0 Hz, 1H), 6.80 (d, J=6.5 Hz, 1H), 4.75 (qd, J=7.5, 6.5 Hz, 1H), 3.80 (s, 3H), 1.53 (d, J=7.5 Hz, 3H).

HRMS Calcd for $C_{15}H_{11}NO_5S_2$: 349.0079, Found: 350.0159 ($MH^+$, FAB).

mp=216.8~217.7° C.

EXAMPLE 37

(L)-2-{(4,8-Dioxo-4,8-dihydrobenzo-[1,2-b;4,5-b'] dithiophene-2-carbonyl)-amino}-propionic acid XVI

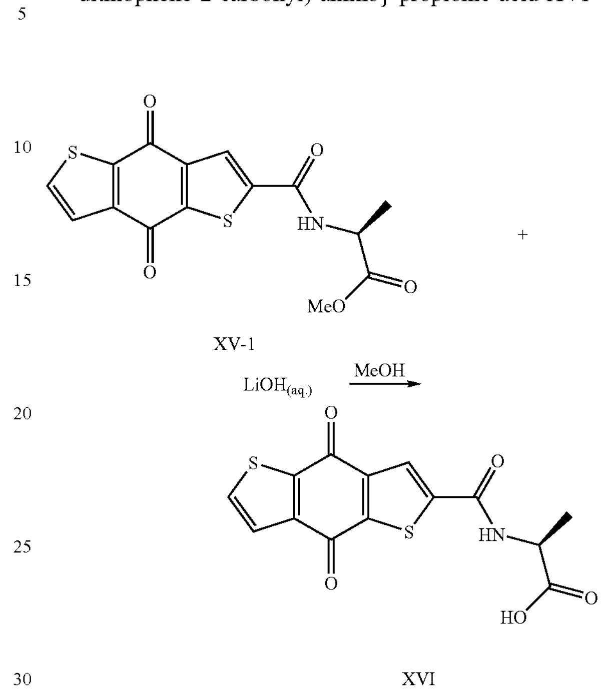

In a 25 mL flask were placed compound XV-1 (17.6 mg, 0.05 mmole) and MeOH (5 ml). LiOH (45.0 mg) in $H_2O$ (4 ml) was then added and reaction mixture stirred at R.T. until hydrolysis completed. HOAc (~0.14 ml) was added drop-wise to neutralize. MeOH was removed under vacuum and the residue was treated with aq. $Na_2CO_3$ and then extracted with EA. The aqueous layer was acidified with dilute HCl solution until pH~4 and the extracted with EA. The EA layer was dried with $Na_2SO_4$, filtered and concentrated to obtain yellow solid XVI (16.8 mg, 99%).

$^1$H NMR (500 MHz, $CDCl_3$) δ 7.96 (s, 1H), 7.62 (d, J=5.0 Hz, 1H), 7.47 (d, J=5.0 Hz, 1H), 4.47 (q, J=7.5 Hz, 1H), 1.36 (d, J=7.5 Hz, 3H).

mp=227.4~228.3° C.

EXAMPLE 38

Sodium (L-2-{(4,8-dioxo-4,8-dihydrobenzo-[1,2-b;4,5-b']dithiophene-2-carbonyl)-amino}-propionate XVI-Na

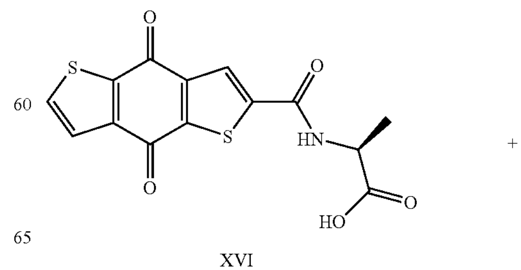

-continued

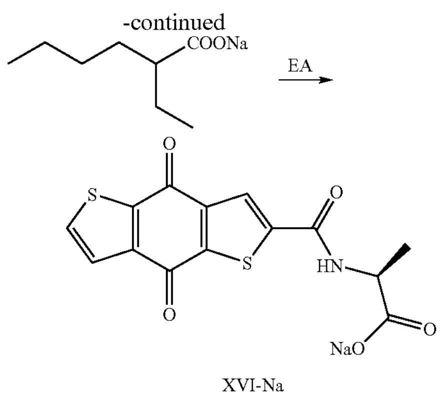

XVI-Na

To a stirred solution of XVI (73.8 mg, 0.22 mmole) in EA was added sodium 2-ethylhexanoate (1.2~1.5 eq.) in EA and stirred for overnight. The precipitate was filtered and washed with EA and then dried in vacuum. Yellow-green solid XVI-Na (47.5 mg, 60% ) was obtained.

$^1$H NMR (500 MHz, $CD_3OD$) δ 8.25 (s, 1H), 7.96 (d, J=5.0 Hz, 1H), 7.65 (d, J=5.0 Hz, 1H), 4.43 (q, J=7.0 Hz, 1H), 1.48 (d, J=7.0 Hz, 3H).

mp>275° C.

EXAMPLE 39

4,8-dioxo-4,8-dihydrobenzo[1,2-b;4,5-b'] dithiophene-2-carboxylate-(2-dimethylamino-ethyl)-amide XV-2

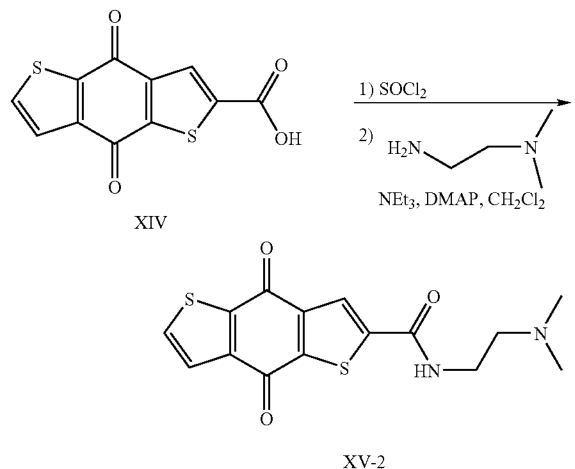

Compound XIV (0.6086 g, 2.0 mmole), $SOCl_2$ (50 ml) along with a small amount of NaCl was heated to reflux for 2 hrs. The excess $SOCl_2$ was removed and $CH_2Cl_2$ was added to the residue. NaCl was filtered and the filtrate was concentrated to yield crude acid chloride (0.5453 g). The acid chloride obtained was used directly without purification. It was diluted with $CH_2Cl_2$ (40 ml) and added to the N,N-dimethylethylenediamine (16 ml), $Et_3N$ (20 ml) and $CH_2Cl_2$ (40 ml) mixture and stirred at R.T. for 12 hrs. Water was added and the reaction mixture extracted with CH2Cl2 The $CH_2Cl_2$ layer was concentrated and crude product was purified through column using MeOH: $CH_2Cl_2$=1:10 as the eluent. Yellow solid XV-2 (255.2 mg, 33%) was obtained.

$^1$H NMR (500 MHz, $CD_3OD$) δ 8.13 (s, 1H), 7.97 (d, J=5.0 Hz, 1H), 7.65 (d, J=5.0 Hz, 1H), 3.55 (t, J=6.5 Hz, 2H), 2.65 (t, J=6.5 Hz, 2H), 2.37 (s, 6H).

HRMS Calcd for $C_{15}H_{14}N_2O_3S_2$: 334.0446, Found: 334.0641.

mp=235.5~236.2° C.

EXAMPLE 40

4,8-dioxo-4,8-dihydrobenzo[1,2-b;4,5-b'] dithiophene-2-carboxylate-(2-dimethyl-aminoethyl)-amide phosphoric acid salt XV-2-$H_3PO_4$

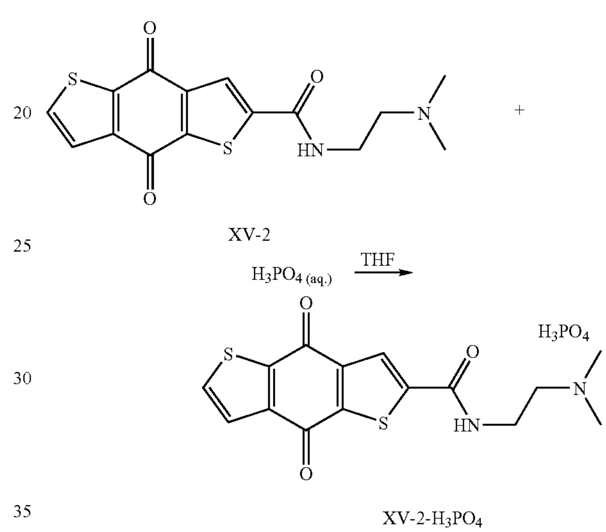

To a stirred solution of XV-2 (100 mg, 0.30 mmole) in THF was added 85% $H_3PO_4$ (1.2~1.5 eq.) and stirred for overnight. The precipitate was filtered and washed with THF and then dried in vacuum. Yellow solid XV-2-$H_3PO_4$ (120 mg, 93%) was obtained.

$^1$H NMR (500 MHz, $D_2O$) δ 8.02 (br, 1H), 7.82 (br, 1H), 7.54 (br, 1H), 3.88 (br, 2H), 3.52 (br, 2H), 3.08 (br, 6H).

mp=233° C. (decomp.)

Cytotoxicity Assays Method A (HUVEC, MCF-7, HT-29, Hep 3B and NCl-H460) [S. A. Ahmed, R. M. Gogal Jr., and J. E. Walsh, Journal of Immunological Methods 170: 211-224, (1994): M. R. Boyd, Status of the NCl preclinical antitumor drug discovery screen. (Published by J. B. Lippincoft Company, Philadelphia, Pa. 19105, USA) Principles & Practices of Oncology Updates 3 # 10: 1-12, (1989); M. R. Boyd, et al. Data display and analysis strategies for the NCl disease-oriented in vitro antitumor drug screen. In: Cytotoxic anti-cancer drugs: models and concepts for drug discovery and development. Boston: Kluwer Academic, Pages; 11-34, (1992)]

1. Materials and Equipment (1) Test Substance and Dosing Pattern

The test compounds were dissolved in 100% DMSO and then diluted with sterile distilled water to obtain initial working solutions of 20000, 2000, 200, 20 and 2 μM in 80% DMSO. A 200 fold dilution was further made in culture media to generate final assay concentrations of 100, 10, 1, 0.1 and 0.01 μM in 0.4% DMSO.

(2) Cell Culture Media

| Cell Lines | Culture Medium |
|---|---|
| HUVEC | Endothelial Cell Growth Medium, 90%; Fetal Bovine Serum, 10% |
| MCF-7 | Minimum Essential Medium, 90%; Fetal Bovine Serum, 10% |
| HT-29 | McCoy's 5A medium, 90%; Fetal Bovine Serum, 10% |
| Hep 3B | Minimum Essential Medium, 90%; Fetal Bovine Serum, 10% |
| NCI-H460 | RPMI 1640, 90%; Fetal Bovine Serum, 10% |

All of media were supplemented with 1% Antibiotic-Antimycotic.

(3) Cell Lines

| Cell Name | Source | Type of Cell Line |
|---|---|---|
| HUVEC | ATCC CRL-1730 | Human umbilical vein endothelial cells |
| MCF-7 | ATCC HTB-22 | Breast adenocarcinoma, pleural effusion, human |
| HT-29 | ATCC HTB-38 | Adenocarcinoma, colon, moderately well-differentiated grade II, human |
| Hep 3B | ATCC HB-8064 | Hepatocellular carcinoma, liver, human |
| NCI-H460 | ATCC HTB-177 | Large cell carcinoma, lung, human |

All of the human tumor cell lines and HUVEC were obtained from American Type Culture Collection (ATCC). The cells were all incubated at 37° C. with 5% $CO_2$ in air atmosphere.

(4) Chemicals

AlamarBlue (Biosource, USA), Antibiotics-Antimycotic (GIBCO BRL, USA), Dimethylsulfoxide (Merck, Germany), Endothelial Cell Growth Medium (CELL APPLICATIONS, INC., USA), Fetal Bovine Serum (HyClone, USA), McCoy's 5A Medium (GIBCO BRL. USA), Minimum Essential medium (GIBCO BRL, USA), Mitomycin (Kyowa, Japan) and RPMI 1640 (HyClone, USA).

(5) Equipment $CO_2$ Incubator (Forma Scientific Inc., USA), Centrifuge 5810R (Eppendorf, Germany), Hemacytometer (Hausser Scientific Horsham, USA), Inverted Microscope CK-40 (Olympus, Japan), System Microscope E-400 (Nikon, Japan), Spectrafluor Plus (Tecan, Austria) and Vertical Laminar Flow (Tsao Hsin, R. O. C.).

2. Methods (1) Evaluation of Anti-Proliferative Activity for Test Substances

Aliquots of 100 μl of cell suspension (about 1.5-3.0×$10^3$/well) were placed in 96-well microtiter plates in an atmosphere of 5% $CO_2$ at 37° C. After 24 hours, 100 μl of growth medium and 1 μl of test solution or vehicle (80% DMSO) were added respectively per well in duplicate for an additional 72-hour incubation. Thus, the final concentration of DMSO was 0.4%. The test compounds, IIa-1, IIb-1 and VII-1 were evaluated at concentrations of 100, 10, 1, 0.1 and 0.01 μM. At the end of incubation, 20 μl of alamarBlue 90% reagent was added to each well for another 6-hour incubation before detection of cell viability by fluorescent intensity. Fluorescent intensity was measured using a Spectraflour Plus plate reader with excitation at 530 nm and emission at 590 nm.

(2) Determination of $IC_{50}$, TGI and $LC_{50}$

The measured results was calculated by the following formula:

$$PG(\%)=100\times(\text{Mean }F_{test}-\text{Mean }F_{time0})/(\text{Mean }F_{ctrl}-\text{Mean }F_{time0})]$$

$$\text{If}(\text{Mean }F_{test}-\text{Mean }F_{time0})<0,\text{ then}$$

$$PG(\%)=100\times(\text{Mean }F_{test}-\text{Mean }F_{time0})/(\text{Mean }F_{time0}-\text{Mean }F_{blank})$$

wherein PG represents percent growth;

Mean $F_{time0}$=The average of 2 measured fluorescent intensities of reduced alamarBlue at the time just before exposure of cells to the test substance;

Mean $F_{test}$=The average of 2 measured fluorescent intensities of alamarBlue after 72-hour exposure of cells to the test substance;

Mean $F_{ctrl}$=The average of 2 measured fluorescent intensities of alamarBlue after 72-hour incubation without the test substance;

Mean $F_{blank}$=The average of 2 measured fluorescent intensities of alamarBlue in medium without cells after 72-hour incubation.

A decrease of 50% or more (≧50%) in fluorescent intensity relative to the vehicle-treated control indicates significant cytostatic or cytotoxic activity, and semi-quantitative values for $IC_{50}$, TGI and $LC_{50}$ were then determined by nonlinear regression using GraphPad Prism (GraphPad Software, USA).

$IC_{50}$ (50% Inhibition Concentration); Test compound concentration where the increase from times in the number or mass of treated cells was only 50% as much as the corresponding increase in the vehicle-control at the end of experiment.

TGI (Total Growth Inhibition): Test compound concentration where the number or mass of treated cells at the end of experiment was equal to that at $time_0$.

$LC_{50}$ (50% Lethal Concentration): Test compound concentration where the number or mass of treated cells at the end of experiment was half that at time.

Cytotoxicity Assays Method B (HL-60) [H. M. Chen et al. *Chin. Pharm. J.* 53, 157-167 (2001)]

Cells and Culture

Human promyeloid leukemia HL-60 cells were obtained from the American Type

Culture Collection (Manassas, Va., USA) and the Culture Collection and Research Center(CCRC) (Tai wan, ROC). Human promyeloid leukemia HL-60 cells were cultured in suspension in RPMI-1640 medium (GIBCO, Grand Is land, USA), containing 10% fetal bovine se rum (GIBCO, Grand Is land, USA), 100 unit/mL penicillin, 100 mL/mL streptomycin and 1% L-glutamine at 37° C. in a humidified atmosphere of 5% CO2 in air. Cells were split every day to maintain the cell numbers between 2–5×$10^5$/mL. Cell numbers were assessed by the standard procedure of leukocyte counting using a hemocytometer and cell viability was checked by the ability of cells to exclude Trypan blue.

MTT Proliferation Assay

Cellular proliferation was determined by the MTT [3-(4, 5-dimethylthiazol-2-yl)-2,5-diphenyltetrazolium bromide] as say. Briefly, 10 mL of MTT (5 mg/mL) was added to each well of 96-well plates containing 1×$10^5$ cells after treatment with different concentrations of samples for 4 days. The reaction was stopped after 2 h by adding 100 mL of 0.04 N HCl in isopropanol and the OD570 nm was determined by a minicolorimetric reader. Each concentration treatment was performed in triplicate.

Cytotoxicity Assays Method C (KB, KB-VIN, AS49, HCT-8, PC-3) [K. H. Lee et. al. Planta Med. 54, 308-312 (1998), Monk A et. al. J. Natl. Cancer Inst. 83, 757-766 (1991).] The cell lines included epidermoid caninoma of the nasopharynx (KB), p-gp-expressing epidermoid caninoma of the nasopharynx (KB-VIN), lung carcinoma (A-549), ileocecal carinoma (HCT-8) and prostate cancer (PC-3) cell lines. The cytotoxic effects of each compounds were obtained as $IC_{50}$ in microgram per ml, the concentration that give 50% inhibition of cell growth after 72 hrs of continuous exposure-variation was less than 5% between replicates.

Anticancer Activity

The assays were used to detect changes in cell proliferation based on the ability of viable cells to cause alamarBlue to change from its oxidized to a reduced form. With the results obtained from the alamarBlue reaction, cell proliferation can be quantified and metabolic activity of viable cell can be examined.

The succinate derivatives of compounds IIa-1, IIb-1 and VII-1 were tested for possible effect on the proliferation of four human tumor cell lines ~MCF-7 (breast), HT-29 (colon), Hep3B (liver), and NCl—H 460 (lung) as well as one human umbilical vein endothelial cell (HUVEC) at assay concentration from 0.01 to 100 μM, through serial 10-fold dilution.

The $IC_{50}$ (50% inhibition concentration), TGI (total growth inhibition) and $LC_{50}$ (50% lethal concentration) of the three tested compounds were summary in Table 1.

As shown in Table 1, the three tested compounds showed potent cytotoxicity in vitro against NCl—H 460 cell line. Compounds IIa-1 and IIb-1 also had significant activity against MCF-7 and Hep3B cell lines. These two compounds displayed moderate and little activity against HT-29 cell line. Compound VII-1 showed significant cytotoxicity against MCF-7 and Hep3B and moderate activity against HT-29 cell line. On the other hand, all the three tested compounds were essentially inactive or showed little activity in HUVEC assay.

Compound IIa-1-IIa-2-IIb-1-IIb-2-VII-1-VII-2-IX and XV-2-$H_3PO_4$ were evaluated for their cytotoxicity in vitro against human promyelocytic leukemia (HL-60) cell line. As shown in Table 2. All of these tested compounds showed significant cytotoxicity. Among them, XV-2-$H_3PO_4$ was the most potent one. There fore this compound was selected for further evaluation.

Mono-[1-(4,8dioxo-4,8-dihydrobenzo[1,2-b:5,4-b'] dithiophen-2-yl)-methyl]succinate (IIa-1), mono-[1-(4,8-dioxo-4,8-dihydrobenzo[1,2-b:5,4-b']dithiophen-2-yl)-methyl]pentanedioate (IIa-2), mono-[1-(4,8-dioxo-4,8-dihydrobenzo[1,2-b:5,4-b']dithiophen-2-yl)-ethyl]succinate (IIb-1), mono-[1-(4,8dioxo-4,8-dihydrobenzo[1,2-b:5,4-b'] dithiophen-2-yl)-ethyl]pentanedioate (IIb-2), ethyl 4,8-dioxo-4,8-dihydroxybenzo[1,2-b:5,4-b']-dithiophen-2-yl-methoxy acetate (IVa), mono-[1-(4,8-dioxo-4,8-dihydroxybenzo[1,2-b;4,5-b']dithiophen-2-yl)-ethyl] succinate (VII-1), mono-[1-(4,8-dioxo-4,8-dihydroxybenzo [1,2-b;4,5-b']dithiophen-2-yl)-ethyl]pentanedioate (VII-2), 1-(4,8-Dioxo-4,8-dihydroxybenzo[1,2-b:4,5-b']-dithiophen-2-yl-ethoxy)-acetate (IX), 4,8-dioxo-4,8-dihydrobenzo-[1,2-b;5,4-b']dithiophene-2-carboxylic acid (XI), 4,8-dioxo-4,8-dihydrobenzo-[1,2-b;4,5-b']dithiophene-2-carboxylic acid (XIV), 4,8-dioxo-4,8-dihydrobenzo-[1,2-b;4,5-b'] dithiophene-2-carboxylate-(2-dimethylamino-ethyl)-amide phosphate (XV-2-$H_3PO_4$), (L)-2-{(4,8-Dioxo-4,8-dihydrobenzo-[1,2-b;4,5-b']dithiophene-2-carbonyl)-amino}-propionic acid (XVI), and their salts were evaluated for their cytotoxicity in vitro against epidermal carcinoma of the nasopharynx (KB), p-gp-expressing epidermoid carcinoma of the nasopharynx (KB-VIN), lung carcinoma (A-549), ileocecal carcinoma (HCT-8) and prostate cancer (PC-3). As shown in Table 2, Most of these tested compounds showed significant cytotxicity. Among them, XV-2-$H_3PO_4$ was the most promising agent. In addition, compounds IIb-1, IIb-2, VII-1 and VII-2 displayed potent activity against the MDR cell line (KB-VIN) and the androgen-insensitive prostate cancer cell line (PC-3). Therefore, compounds XV-2-$H_3PO_4$, IIb-1, IIb-2 VII-1 and VII-2 were selected for further pharmacological studies. In summary, the present invention demonstrated remarkable therapeutical potential for benzodithiophenone analogs in the treatment of cancers.

The present invention also discloses a hydrophilic compound having the following structures (F) or (G), or a pharmaceutically acceptable salt thereof:

(F)

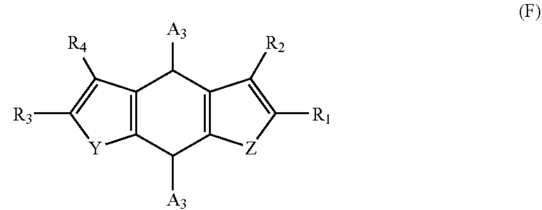

(G)

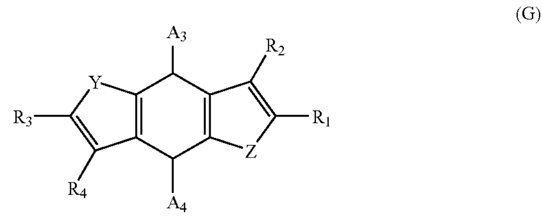

wherein $A_3$ and $A_4$ independently are —U—C(O)—$(CH_2)_n$ COOH, —U—$(CH_2)_n$—COOH, —U$(CH_2)_n$—$NR_5R_6$,

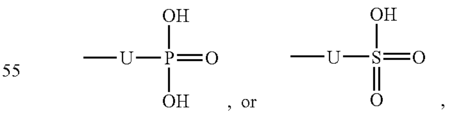

wherein U is O, S, or NH, $R_5$ is H or alkyl; $R_6$ is H or alkyl; and n is 1-5; and Y, Z, $R_1$, $R_2$, $R_3$ and $R_4$ are defined as above.

The present invention also discloses a method for treating a tumor, said method comprising administering to a subject in need of treatment a compound having the formulas (F) or (G) as defined above, or a pharmaceutically acceptable salt thereof, in an amount effective to treat said tumor.

TABLE 1

Cytotoxicity of compounds IIa-1, IIb-1, and VII-1 against MCF7, HT-29, Hep-3B, NCI-H460 and HUVEC cell lines IIa-1, R = $CH_2$—$OCO(CH_2)_2COOH$
IIb-1, R = $CH(CH_3)$—$OCO(CH_2)_2COOH$

VII-1, R = $CH(CH_3)$—$OCO(CH_2)_2COOH$

| | HUVEC | | | MCF-7 | | | HT-29 | | | Hep-3B | | | NCI-H460 | | |
|---|---|---|---|---|---|---|---|---|---|---|---|---|---|---|---|
| Compounds | $IC_{50}$[a] | TGI[b] | $LC_{50}$[c] | $IC_{50}$[a] | TGI[b] | $LC_{50}$[c] | $IC_{50}$[a] | TGI[b] | $LC_{50}$[c] | $IC_{50}$[a] | TGI[b] | $LC_{50}$[c] | $IC_{50}$[a] | TGI[b] | $LC_{50}$[c] |
| IIa-1 | 10 | 19 | 34 | 3.4 | 6.9 | 14 | 11 | 22 | 45 | 2.8 | 5.1 | 9.2 | 0.81 | 1.7 | 3.5 |
| IIb-1 | 11 | 31 | 89 | 0.82 | 4.7 | 27 | 4.3 | 2.0 | 89 | 1.1 | 1.8 | 2.9 | 0.64 | 1.2 | 2.1 |
| VII-1 | 11 | 57 | >100 | 0.96 | 5.5 | 31 | 4.5 | 38 | >100 | 1.0 | 1.9 | 3.4 | 0.41 | 1.1 | 3.0 |

[a]$IC_{50}$ (50% Inhibition Concentration): Test compound concentration μM where the increase from $time_0$ in the number or mass of treated cells was only 50% as much as the corresponding increase in the vehicle-control at the end of experiment.
[b]TGI (Total growth Inhibition): Test compound concentration μM where the number or mass of treated cells at the end of experiment was equal to that at $time_0$.
[c]$LC_{50}$ (50% Lethal Concentration): Test compound concentration μM where the number or mass of treated cells at the end of experiment was half that at $time_0$.

TABLE 2

Cytotoxicity of compounds IIa-1, IIa-2, IIb-1, IIb-2, VII-1, VII-2, IX and XV-2-$H_3PO_4$ against HL-60 cell line[a].

IIa-1, IIa-2
IIb-1, IIb-2

VII-1, VII-2
IX, XV-2-$H_3PO_4$

| Compound | R | $IC_{50}$ (uM)[b] |
|---|---|---|
| IIb-1 | —$CH(CH_3)$—$OCO(CH_2)_2COOH$ | 0.26 |
| IIb-2 | —$CH(CH_3)$—$OCO(CH_2)_3COOH$ | 0.25 |
| IIa-1 | —$CH_2$—$OCO(CH_2)_2COOH$ | 0.47 |
| IIa-2 | —$CH_2$—$OCO(CH_2)_3COOH$ | 0.70 |
| VII-1 | —$CH(CH_3)$—$OCO(CH_2)_2COOH$ | 0.26 |
| VII-2 | —$CH_2$—$OCO(CH_2)_3COOH$ | 0.28 |
| XVI | —$CONHCH(CH_3)COOH$ | 0.75 |
| IX | —$CH(CH_3)OCH_2COOH$ | 2.58 |
| XV-2-$H_3PO_4$ | —$CONH(CH_2)_2N(CH_3)_2H_3PO_4$ | 0.05 |

[a]Human promyielocytic leukemia (HL-60).

[b]$IC_{50}$ values are the concentration at which 50% of the cells are inhibited from growing.

TABLE 3

Cytotoxicity of compounds IIa-1, IIa-2, IIb-1, IIb-2, IVa, VII-1, VII-2, IX, XI, IV, XV, XVI and their salts against KB, KB-VIN, A-549, HCF-8 and PC-3 cell lines.

IIa-1, IIa-2
IIb-1, IIb-2

VII-1, VII-2
IX, XV-2-$H_3PO_4$

| | | $IC_{50}$ (uM)[a] | | | | |
|---|---|---|---|---|---|---|
| Compound | R | KB[b] | KB-VIN[c] | A549[d] | HCT-8[e] | PC-3[f] |
| IIb-1 | —$CH(CH_3)$—O—CO—$(CH_2)_2COOH$ | 0.47 | 0.25 | 0.58 | 0.91 | 0.22 |
| IIb-1-Na | —$CH(CH_3)$—O—CO—$(CH_2)_2COONa$ | 0.55 | 0.47 | 0.47 | 1.83 | 0.37 |

TABLE 3-continued

| | | | | | | |
|---|---|---|---|---|---|---|
| IIb-2 | —CH($CH_3$)—O—CO—($CH_2$)$_3$COOH | 0.03 | 0.05 | 0.11 | 0.19 | 0.06 |
| IIb-2-Na | —CH($CH_3$)—O—CO—($CH_2$)$_3$COONa | 1.36 | 1.13 | 1.89 | 1.89 | 0.88 |
| IIa-1 | —$CH_2$—O—CO—($CH_2$)$_2$COOH | 2.02 | 4.47 | 4.03 | 4.03 | 1.35 |
| IIa-1-Na | —$CH_2$—O—CO—($CH_2$)$_2$COONa | 2.09 | 3.79 | 3.79 | 3.25 | 1.22 |
| IIa-2 | —$CH_2$—O—CO—($CH_2$)$_3$COOH | 2.22 | 1.39 | 2.08 | 1.66 | 0.75 |
| IIa-2-Na | —$CH_2$—O—CO—($CH_2$)$_3$COONa | 1.72 | 1.31 | 0.94 | 0.65 | 0.89 |
| IVa | —$CH_2$—O—$CH_2$COOH | 3.61 | 2.46 | 2.46 | 2.07 | 1.05 |
| XI | —COOH | 38.31 | 38.31 | 30.27 | 37.16 | 13.41 |
| XI-$NH_4$ | —$COONH_4$ | 35.97 | 35.97 | >70 | >70 | >70 |
| VII-1 | —CH($CH_3$)—OCO—($CH_2$)$_2$COOH | 0.19 | 0.22 | 0.47 | 0.42 | 0.16 |
| VII-1-Na | —CH($CH_3$)—OCO—($CH_2$)$_2$COONa | 2.14 | 1.96 | 2.22 | 1.44 | 0.73 |
| VII-2 | —CH($CH_3$)—OCO—($CH_2$)$_3$COOH | 0.08 | 0.24 | 0.51 | 0.48 | 0.06 |
| VII-2-Na | —CH($CH_3$)—OCO—($CH_2$)$_3$COONa | 0.45 | 0.68 | 2.52 | 0.88 | 0.10 |
| XIV | —COOH | 38.31 | 38.31 | 44.44 | 44.06 | 25.29 |
| XIV-$NH_4$ | —$COONH_4$ | 35.97 | 35.97 | 16.19 | 26.26 | 13.31 |
| XV-2-$H_3PO_4$ | —CONH($CH_2$)$_2$—N($CH_3$)$_2$—$H_3PO_4$ | 0.06 | 0.01 | 0.01 | 0.01 | 0.01 |
| XVI-Na | —CONH—C($CH_3$)COONa | 1.76 | 0.54 | 0.54 | 0.51 | 0.17 |
| IX | —CH($CH_3$)—O—$CH_2$COOH | 19.75 | 18.18 | 2.60 | 0.24 | 2.51 |
| IX-Na | —CH($CH_3$)—O—$CH_2$COONa | 1.11 | 1.00 | 0.26 | 0.22 | 0.14 |
| | Doxorubincin | 0.18 | 4.97 | 0.18 | ND[g] | ND[g] |
| | VP-16 | 4.76 | >10 | 1.36 | ND[g] | ND[g] |
| | VCR | 0.01 | 5.33 | 0.04 | ND[g] | ND[g] |

[a]$IC_{50}$ was the concentration of compound which afforded 50% reduction in cell number after 72 hr of incubation.
[b]epidermoid carcinoma of the nasopharynx (KB).
[c]p-gp-expressing epidermoid carcinoma of the nasopharynx (KB-VIN).
[d]lung carcinoma (A-549).
[e]ileocecal carcinoma (HCT-8).
[f]prostate cancer (PC-3).
[g]ND = Not active at 20 mcq/mL.

The water solubility of some of the synthesized compounds were tested and summarized as below.

| Compound | Solubility |
|---|---|
| 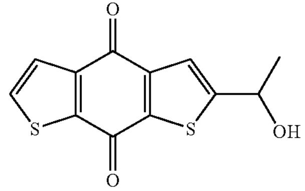 1b | $9.6 \times 10^{-3}$ mg/1 mL $H_2O$ |
| 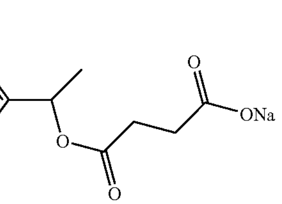 IIb-1-Na | ≧3 mg/1 mL $H_2O$ |
| 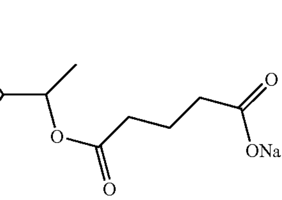 IIb-2-Na | ≧9.6 mg/1 mL $H_2O$ |

-continued
| Compound | Solubility |
| --- | --- |
| 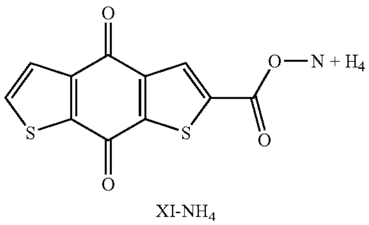XI-$NH_4$ | ≧10 mg/1 mL $H_2O$ |
| 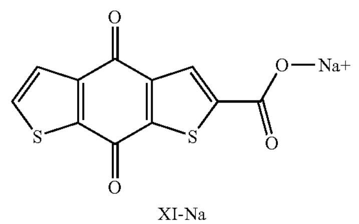XI-Na | ≧10 mg/1 mL $H_2O$ |
| 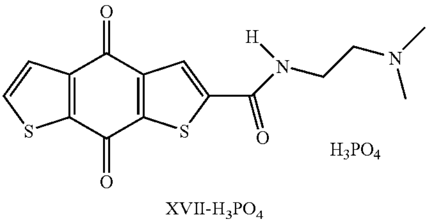XVII-$H_3PO_4$ | ≧2 mg/1 mL $H_2O$ |
| 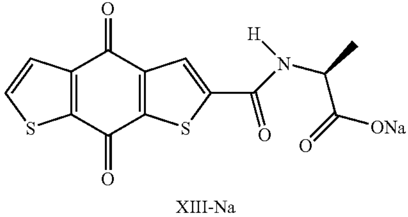XIII-Na | ≧6.6 mg/1 mL $H_2O$ |
| 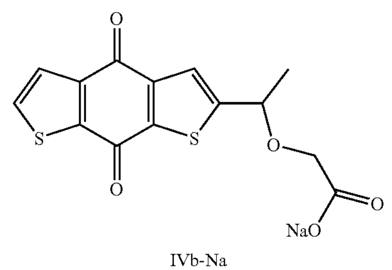IVb-Na | ≧3.2 mg/1 mL $H_2O$ |
| 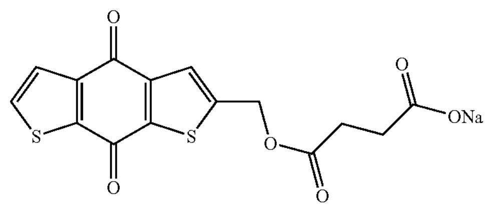IIa-1-Na | ≧10 mg/1 mL $H_2O$ |

-continued
| Compound | Solubility |
| --- | --- |
| 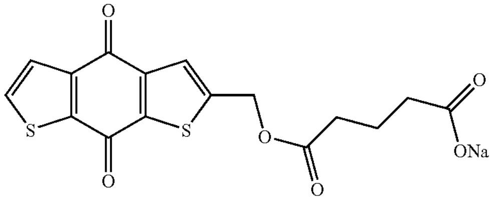<br><br>IIa-2-Na | ≧1.8 mg/1 mL $H_2O$ |
| 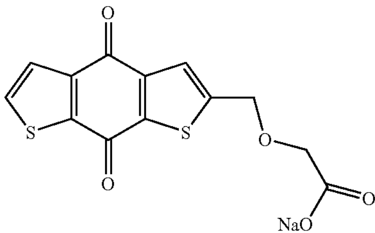<br><br>IVa-Na | ≧9.6 mg/1 mL $H_2O$ |
| 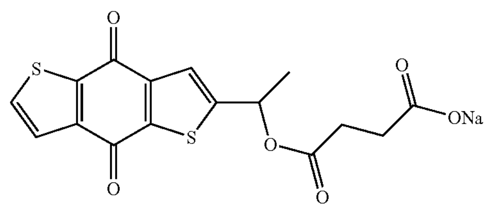<br><br>VII-1-Na | ≧10 mg/1 mL $H_2O$ |
| 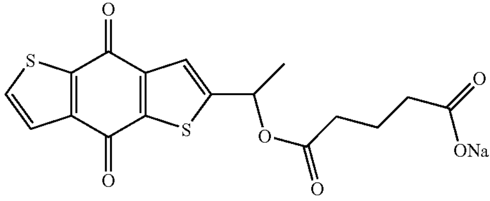<br><br>VII-2-Na | ≧3.4 mg/1 mL $H_2O$ |
| 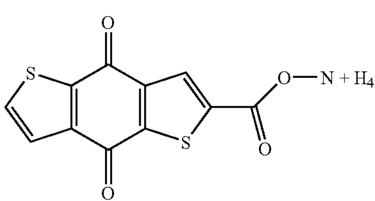<br><br>XIV-$NH_4$ | ~4 mg/1 mL $H_2O$ |
| 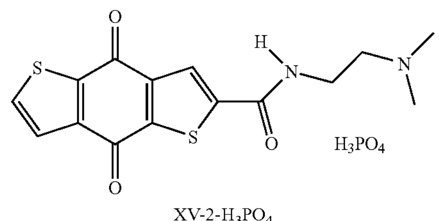<br><br>XV-2-$H_3PO_4$ | ≧4 mg/1 mL $H_2O$ |

-continued

| Compound | Solubility |
|---|---|
| 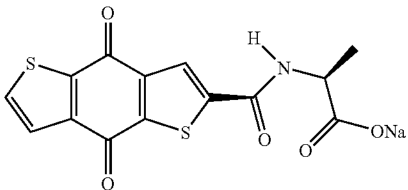 XVI-Na | ≧3.2 mg/1 mL $H_2O$ |
| 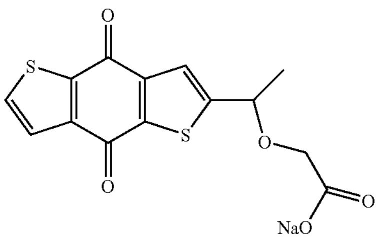 IX-Na | ≧6 mg/1 mL $H_2O$ |

We claim:

1. A derivative of 4,8-dihydrobenzodithiophene-4,8-dione having the formulas (D) or (E):

(D)

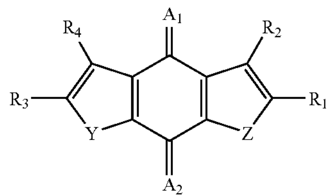

(E)

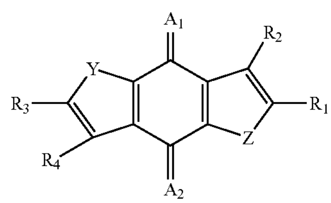

wherein Y and Z independently are O, S, —NH— or Se;

$A_1$ and $A_2$ independently are O, S, and $NR_5$, wherein $R_5$ is H or alkyl;

$R_1$, $R_2$, $R_3$, and $R_4$ independently are H, alkyl, —$CR_5R_6$—X—C (O)—$(CH_2)_n$COOH, —$CR_5R_6$—X—$(CH_2)_n$COOH, —$CR_5R_6$—X—$(CH_2)_n NR_5R_6$, —C (O)—$NR_6$—$(CR_5R_6)_n$COOH, —C (O)—$NR_6$—$(CR_5R_6)_n NR_5R_6$, —$CR_5R_6$—C (O)—$(CH_2)_n$COOH, $CR_5R_6$—X—C (O)—$(CH_2)_n NR_5R_6$, —C (O)—$(CR_5R_6)_n$COOH, —C (O)—$(CR_5R_6)_n NR_5R_6$, —$CR_5$=N—$(CH_2)_n$COOH, —$CR_5$=N—$(CH_2)_n$ COOH, —$CR_5$=NO, or

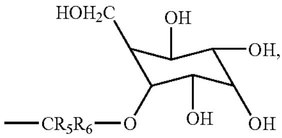

wherein X is O, S, or NH; $R_5$ is defined as above; $R_6$ is H or alkyl; and n is 1-5; subject to the proviso that at least one of $R_1$, $R_2$, $R_3$, and $R_4$ is a radical other than hydrogen and alkyl; or a pharmaceutically acceptable salt thereof.

2. The derivative as defined in claim 1, wherein $R_2$, $R_3$ and $R_4$ are H and $R_1$ is —$CR_5R_6$—X—C (O)—$(CH_2)_n$COOH, —$CR_5R_6$—X—$(CH_2)_n$COOH, —$CR_5R_6$—X—$(CH_2)_n NR_5R_6$, —C (O)—$NR_6$—$(CR_5R_6)_n$COOH, or —C (O)—$NR_6$—$(CR_5R_6)_n NR_5R_6$, wherein $XR_5$, $R_6$ and n are defined as in claim 1.

3. The derivative as defined in claim 1, wherein Y and Z are S.

4. The derivative as defined in claim 2, wherein Y and Z are S.

5. The derivative as defined in claim 1, wherein $A_1$ and $A_2$ are O.

6. The derivative as defined in claim 2, wherein $A_1$ and $A_2$ are O.

7. The derivative as defined in claim 3, wherein $A_1$ and $A_2$ are O.

8. The derivative as defined in claim 4, wherein $A_1$ and $A_2$ are O.

9. The derivative as defined in claim 8, wherein X is O.

10. The derivative as defined in claim 9, wherein $R_5$ and $R_6$ independently are H or methyl.

11. The derivative as defined in claim 10, wherein $R_1$ is —$CR_5R_6$—X—C (O)—$(CH_2)_n$COOH.

12. The derivative as defined in claim 10, wherein $R_1$ is —$CR_5R_6$—X—$(CH_2)_n$COOH.

13. The derivative as defined in claim 10, wherein $R_1$ is —$CR_5R_6$—X—$(CH_2)_nNR_5R_6$.

14. The derivative as defined in claim 10, wherein $R_1$ is —C (O)—$NR_6$—$(CR_5R_6)_n$COOH.

15. The derivative as defined in claim 10, wherein $R_1$ is —C (O)—$NR_6$—$(CR_5R_6)_nNR_5R_6$.

16. The derivative as defined in claim 10 having the formula (D).

17. The derivative as defined in claim 10 having the formula (E).

18. A compound having the following structures (F) or (G):

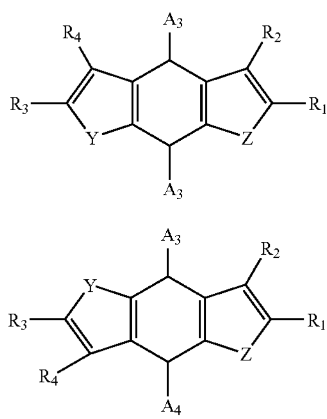

wherein $A_3$ and $A_4$ independently are —U—C (O)—$(CH_2)_n$COOH, —U—$(CH_2)_n$—COOH, —U—$(CH_2)_n$—$NR_5R_6$,

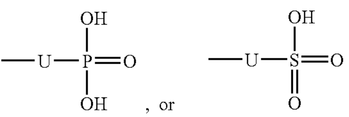

wherein U is O, S, or NH; $R_5$ is H or alkyl; $R_6$ is H or alkyl; and n is 1-5; and Y, Z, $R_1$, $R_2$, $R_3$, and $R_4$ are defined as in claim 1, or a pharmaceutically acceptable salt thereof.

19. The derivative as defined in claim 10, which is mono-[1-(4,8-dioxo-4,8-dihydrobenzo[1,2-b;5,4-b'] dithiophen-2-yl)-methyl]succinate, mono-[1-(4,8-dioxo-4,8-dihydrobenzo[1,2-b:5,4-b']dithiophen-2-yl)-ethyl]succinate, or mono-[1-(4,8-dioxo-4,8-dihydrobenzo[1,2-b:5,4-b'] dithiophen-2-yl)-ethyl]pentanedioate;

mono-[1-(4,8-dioxo-4,8-dihydroxybenzo[1,2-b;4,5-b'] dithiophen-2-yl)-ethyl]succinate, mono-[1-(4,8-dioxo-4,8-dihydroxybenzo[1,2-b;4,5-b']dithiophen-2-yl)-ethyl]pentanedioate, or 4,8-dioxo-4,8-dihydrobenzo[1,2-b;4,5-b']dithiophene-2-carboxylate-(2-dimethylamino-ethyl)-amide.

* * * * *